United States Patent
Wang et al.

(10) Patent No.: US 11,633,134 B2
(45) Date of Patent: Apr. 25, 2023

(54) SELF-POWERED BIOSENSORS

(71) Applicant: The Regents of the University of California, Oakland, CA (US)

(72) Inventors: Joseph Wang, La Jolla, CA (US); Patrick Mercier, La Jolla, CA (US); Ali Fazli Yeknami, La Jolla, CA (US); Somayeh Imani, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/785,507

(22) Filed: Feb. 7, 2020

(65) Prior Publication Data
US 2020/0253520 A1 Aug. 13, 2020

Related U.S. Application Data

(60) Provisional application No. 62/802,576, filed on Feb. 7, 2019.

(51) Int. Cl.
*A61B 5/00* (2006.01)
*A61B 5/1486* (2006.01)
(Continued)

(52) U.S. Cl.
CPC .......... *A61B 5/14865* (2013.01); *A61B 5/002* (2013.01); *A61B 5/14532* (2013.01);
(Continued)

(58) Field of Classification Search
CPC ............ A61B 5/14532; A61B 5/14535; A61B 5/14539; A61B 5/14546; A61B 5/14542;
(Continued)

(56) References Cited

U.S. PATENT DOCUMENTS 7,368,190 B2    5/2008  Heller et al.
10,164,454 B2 * 12/2018 Chatroux ................ H02J 7/345
(Continued)

FOREIGN PATENT DOCUMENTS

WO    2011117357 A2    9/2011

OTHER PUBLICATIONS

Arshak, K. et al., "Conducting polymers and their applications to biosensors: Emphasizing on foodborne pathogen detection", IEEE Sens. J. 2009, 9, 1942-1951.
(Continued)

*Primary Examiner* — Alex M Valvis
*Assistant Examiner* — Aurelie H Tu
(74) *Attorney, Agent, or Firm* — Perkins Coie LLP

(57) ABSTRACT

Disclosed are self-powering biofuel cell and sensor devices, systems and techniques. In some aspects, a self-powered biosensing system includes an electronic circuit; an anode including an enzymatic layer electrically coupled to a power supply voltage terminal of the electronic circuit and configured to interact with an analyte in a fluid, such as glucose or lactate; and a cathode electrically coupled to a ground voltage terminal of the electronic circuit, where the electronic circuit is operable to control and use the electrical energy generated at the anode and cathode for powering the biosensing system and detecting a concentration of the analyte in the fluid.

16 Claims, 34 Drawing Sheets

(51) Int. Cl.
| | |
|---|---|
| *H01M 8/04858* | (2016.01) |
| *G01N 27/327* | (2006.01) |
| *H01M 8/16* | (2006.01) |
| *A61B 5/145* | (2006.01) |

(52) U.S. Cl.
CPC ..... *A61B 5/14546* (2013.01); *G01N 27/3271* (2013.01); *H01M 8/04873* (2013.01); *H01M 8/16* (2013.01); *A61B 2560/0214* (2013.01); *A61B 2562/0285* (2013.01); *A61B 2562/162* (2013.01)

(58) Field of Classification Search
CPC .............. A61B 2562/162; H01M 8/16; H01M 8/04873; H01M 8/04932; G01N 27/3271; G01N 27/3272; G01N 27/3273; G01N 27/3275
See application file for complete search history.

(56) References Cited

U.S. PATENT DOCUMENTS

| | | | |
|---|---|---|---|
| 2005/0255345 A1 | 11/2005 | Gerritse et al. | |
| 2005/0260492 A1 | 11/2005 | Tucholski et al. | |
| 2006/0063043 A1 | 3/2006 | Zeikus et al. | |
| 2008/0044721 A1 | 2/2008 | Heller et al. | |
| 2008/0160384 A1 | 7/2008 | Iqbal et al. | |
| 2009/0082645 A1* | 3/2009 | Hafezi | A61B 5/073 600/302 |
| 2010/0099010 A1 | 4/2010 | Niessen et al. | |
| 2011/0135966 A1 | 6/2011 | Jayaprakash | |
| 2011/0274959 A1 | 11/2011 | Bailey et al. | |
| 2014/0322617 A1* | 10/2014 | Wang | H01M 4/8835 429/401 |
| 2018/0026453 A1* | 1/2018 | Hwang | H02J 7/0048 320/167 |
| 2018/0088535 A1* | 3/2018 | Wang | G04F 10/005 |
| 2018/0233761 A1* | 8/2018 | Slaughter | H01M 8/16 |
| 2019/0342637 A1* | 11/2019 | Halac | A61B 5/14546 |
| 2020/0382106 A1* | 12/2020 | Wang | H03K 3/0231 |

OTHER PUBLICATIONS

Bandodkar et al. "Wearable Chemical Sensors: Present Challenges and Future Prospects" ACS Sensors, 2016, 1(5) pp. 464-482.
Bandodkar et al. "Soft, stretchable, high power density electronic skin-based biofuel cells for scavenging energy from human sweat", Energy & Environmental Science, 2017, vol. 10, pp. 1581-1589.
Barton, S. C. et al., "Enzymatic biofuel cells for implantable and microscale devices", Chem. Rev. 2004, 104, 4867-4886.
Bedekar, A.S. et al., "Oxygen limitation in microfluidic biofuel cells", Chem. Eng. Commun. 2007, 195, 256-266.
Daly et al. "A 6-bit, 0.2V to 0.9V Highly Digital Flash ADC with Comparator Redundancy" ISSCC Dig. Tech. Papers, 2008, pp. 554-555.
Davis, F. et al., "Biofuel cells—recent advances and applications", Biosens. Bioelectron. 2007, 22, 1224-1235.
Gerard, M. et al., "Application of conducting polymers to biosensors", Biosens. Bioelectron. 2002, 17, 345-359.
Goldberg, H. D. et al., "Screen printing: A technology for the batch fabrication of integrated chemical-sensor arrays", Sens. Actuat. B 1994, 21, 171-183.
Kadara, R. O. et al., "Characterization and fabrication of disposable screen printed microelectrodes", Electrochem. Commun. 2009, 11, 1377-1380.
Kim, J. et al., "Challenges in biocatalysis for enzyme-based biofuel cells", Biotechnol. Adv. 2006, 24, 296-308.
S. Imani, et al., "Wearable chemical sensors: Opportunities and challenges," in Proceedings—IEEE International Symposium on Circuits and Systems, 2016, vol. 2016—July.
ISA, International Search Report, International Application No. PCT/US2012/067481, dated Nov. 8, 2013, 12 pages.
Mercier, P. et al. "A sub-nW 2.4 GHz Transmitter for Low Data-Rate Sensing Applications" IEEE J Solid-State Circuits. Jul. 2014; 49(7): 1463-1474.
Metters, J.P. et al., "New directions in screen printed electroanalytical sensors: An overview of recent developments", Analyst 2011, 136, 1067-1076.
Michel, F. et al. "A 250 mV 7.5 µW 61 dB SNDR SC ΔΣ Modulator Using Near-Threshold-Voltage-Biased Inverter Amplifiers in 130 nm CMOS" IEEE Journal of Solid-State Circuits, vol. 47, No. 3, Mar. 2012, pp. 709-721.
Moehlenbrock, M. J. et al., "Extended lifetime biofuel cells", Chem. Soc. Rev. 2008, 37, 1188-1196.
Parashkov, R. et al., "Large area electronics using printing methods", Proc. IEEE 2005, 93, 1321-1329.
Ramanavicius, A. et al., "Enzymatic biofuel cell based on anode and cathode powered by ethanol", Biosens. Bioelectron. 2008, 24, 761-766.
Rogers, J. A. et al., "Printing process suitable for reel-to-reel production of high-performance organic transistors and circuits", Adv. Mater. 1999, 11, 741-745.
Sattayasamitsathit, S. et al., "Highly dispersed Pt nanoparticle-modified 3D porous carbon: A metallized carbon electrode material", Electrochem. Commun. 2011, 13, 856-860.
Smolander, M. et al., "Development of a printable laccase-based biocathode for fuel cell applications", Enzyme Microb. Tech., 2008, 43, 93-102.
Tudorache, M. et al., "Biosensors based on screen-printing technology, and their applications in environmental and food analysis", Anal. Bioanal. Chem. 2007, 388, 565-578.
Wang, J. "Electrochemical glucose biosensors", Chem. Rev. 2008, 108, 814-825.
Yang, X. Y. et al., "Immobilization technology: A sustainable solution for biofuel cell design", Energy Environ. Sci. 2012, 5, 5540-5563.
Yeknami et al. "Low-Power DT ΔΣ Modulator Using SC Passive Filters in 65nm CMOS" IEEE TCAS-I, 2014, vol. 61, No. 2, pp. 358-370.
Yeknami et al., "A 0.3-V CMOS biofuel-cell-powered wireless glucose/lactate biosensing system," IEEE J. Solid-State Circuits, vol. 53, No. 11, 2018. 41 pages.
Yeknami et al., "A 0.3-V CMOS biofuel-cell-powered glucose/lactate biosensing system Employing a 180nW 64dB SNR Passive ΔΣ ADC and a 920MHz Wireless Transmitter," ISSCC 2018, Session 17, pp. 284-285 + supplemental page.
Yu, E. H. et al., "Enzymatic biofuel cells—fabrication of enzyme electrodes", Energies 2010, 3, 23-42.
Zhou, M. et al., "A self-powered 'Sense-Act-Treat' system that is based on a biofuel cell and controlled by Boolean logic", Angew. Chem. Int. Ed. 2012, 51, 2686-2689.
Zhou, M. et al., "Biofuel cells for self-powered electrochemical biosensing and logic biosensing: A review", Electroanal. 2012, 24, 197-209.
Zhou, M. et al., "DNAzyme logic-controlled biofuel cells for self-powered biosensors", Chem. Commun. 2012, 48, 3815-3817.

\* cited by examiner

SELF-POWERED BIOSENSORS

CROSS-REFERENCE TO RELATED APPLICATIONS

This patent document claims priorities to and benefits of U.S. Provisional Patent Application No. 62/802,576, titled "SELF-POWERED BIOSENSORS" and filed on Feb. 7, 2019. The entire content of the aforementioned patent application is incorporated by reference as part of the disclosure of this patent document.

TECHNICAL FIELD

This patent document relates to biosensor and biofuel cell technologies.

BACKGROUND

Sensors based on electrochemical processes can be used to detect a chemical substance or a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

A fuel cell is a device that converts chemical energy from a substance (e.g., referred to as a fuel) into electrical energy (e.g., electricity). Generally, the energy conversion includes a chemical reaction with oxygen or another oxidizing agent. For example, hydrogen is among a common fuel, and hydrocarbons such as natural gas and alcohols can also be used in fuel cells. For example, fuel cells differ from batteries in that they require a constant source of fuel and oxygen to operate, but can produce electricity continually provided the fuel and oxygen inputs are supplied to the fuel cell.

SUMMARY

Disclosed are devices, systems and methods for performing sensing of metabolites while using the power from a biofuel (e.g., the metabolite) to directly power an analog-to-digital converter and wireless transmitter, without requiring any external power source.

Also disclosed are ingestible devices, systems and methods for sensing metabolites while using the power from a biofuel (e.g., the metabolite) to directly power an electric circuit, without requiring any external power source.

In some embodiments in accordance with the disclosed technology, a biosensing system having a biosensor for detecting an analyte or analytes (e.g., glucose or lactate) includes an electronic circuit (e.g., one or more integrated circuits), an anode including a first nanocomposite and an enzymatic layer, where the anode is electrically coupled to a power supply voltage terminal of the electronic circuit and configured to interact with the glucose or lactate, and a cathode including a second nanocomposite electrically coupled to a ground voltage terminal of the electronic circuit, wherein the electronic circuit is configured to use power generated while the analyte, e.g., glucose or lactate, is being transformed to a derivative substance (e.g., gluconolactone and pyruvate, respectively), based on reactions occurring at the modified biosensor electrodes (e.g., including the first nanocomposite of the anode).

In some embodiments in accordance with the disclosed technology, an electronic device powered by biofuel cell includes an enzymatic biofuel cell to extract energy from a biological fluid, and an amplifier circuit powered by the enzymatic biofuel cell. The enzymatic biofuel cell includes an anode disposed on a substrate, the anode including a catalyst to facilitate the conversion of an enzymatic substance in the biological fluid to a first product in an oxidative process that releases electrons captured at the anode, thereby extracting energy from the enzymatic substance, and a cathode disposed on the substrate and separated from the anode, the cathode operable to reduce an oxygenated substance in the biological fluid to a second product in a chemical reduction process in which the second product gains electrons. The amplifier circuit includes a delta-sigma modulation analog-to-digital converter (DSM ADC) operable directly from the energy extracted by the enzymatic biofuel cell, and a switch coupled between the enzymatic biofuel cell and the DSM ADC to supply electrical current from the extracted energy to the amplifier circuit to establish a supply voltage at 0.25 V to 0.4 V.

In some embodiments in accordance with the disclosed technology, an ingestible biofuel cell device includes a capsule including a curved cylindrical body encompassing a hollow interior and an opening at one end of the capsule to the hollow interior; a biofuel cell contained in a first chamber within the hollow interior of the capsule proximate the opening, the biofuel cell operable to extract energy from a metabolite in a fluid of a living organism that ingests the ingestible biofuel cell; and an electronic circuit contained in a second chamber within the hollow interior of the capsule, the electronic circuit including an amplifier and a switch, wherein the electronic circuit is operable to supply electrical current from the extracted energy of the biofuel cell to the amplifier to establish a supply voltage for the device.

The subject matter described in this patent document can be implemented in specific ways that provide one or more of the following features.

DETAILED DESCRIPTION

Figure 1A:
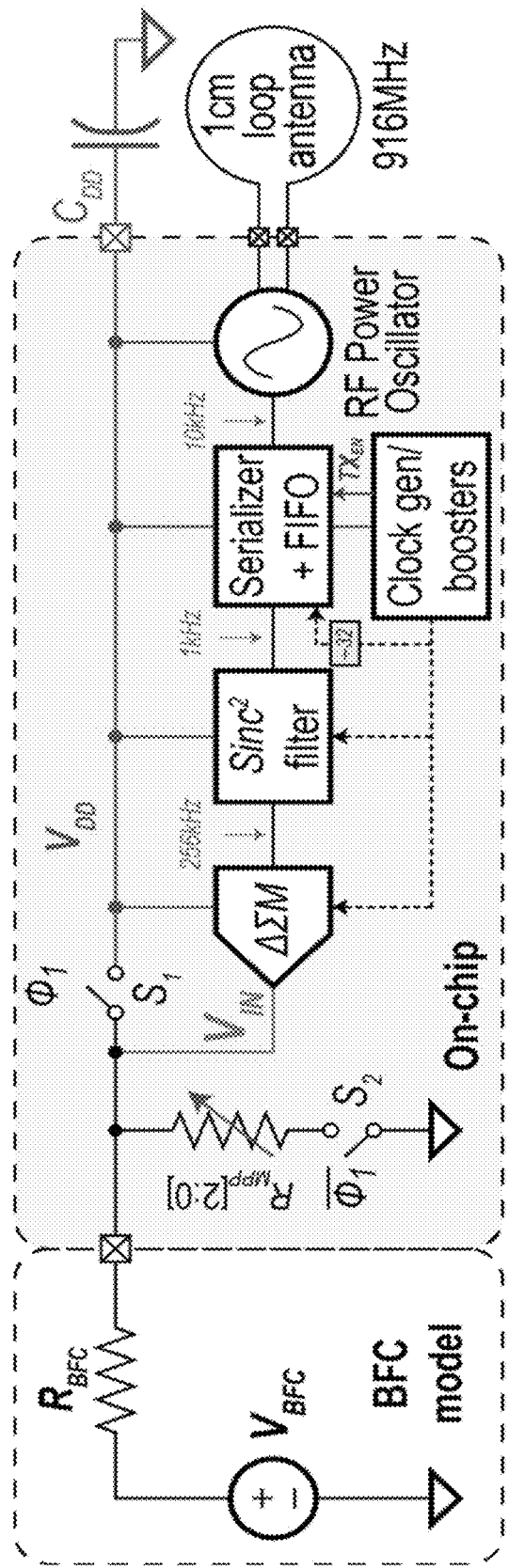
FIG. 1A shows a diagram depicting a system architecture for an example embodiment of a DC-DC-converter-free biofuel-cell (BFC)-powered wireless glucose/lactate biosensor system, in accordance with the present technology.

Wearable physiochemical biosensors offer an exciting opportunity to monitor the concentration of ions and metabolites in bodily fluids such as sweat, saliva, and interstitial fluids for emerging applications in health and fitness monitoring. For example, wearable devices can be designed for monitoring a user's daily physical activities, respiration rate during sleep, or electrophysiological signals such as electrocardiograms (ECG), electroencephalograms (EEG), and electromyograms (EMG). These electrophysiological parameters can offer valuable insight into the status of the human body, but, they by no means offer a complete picture. Thus, alongside more conventional sensing modalities, recent work has attempted to incorporate monitoring of physiochemical quantities in bodily fluids such as sweat, saliva, tears, urine, or interstitial fluid to offer a more comprehensive assessment of a user's current physiological status. For example, physiochemical sensing has been demonstrated for a wide range of applications over a wide range of form factors, for example, ranging from glucose sensing in contact lenses, saliva sensing in a mouthguard, to hybrid sensing of electrophysiology (ECG) and physiochemistry (lactate) in a wearable patch.

Yet, current physiochemical sensing devices rely on batteries and DC-DC converters to provide power for instrumentation. For instance, some biofuel cell (BFC) harvesters utilize bulky boost converters to increase the 0.3-0.4V BFC voltage to a higher level suitable for conventional CMOS circuits. Sometimes those bulky boost converters require unnecessarily large inductors or capacitors, which may result in a large, obtrusive form factor with limited lifetime.

In some examples, conventional wearable devices are powered either from an on-board battery and co-located dc-dc converter, or via a proximal source of wireless power (e.g., via a near-field communication link). Unfortunately, neither power delivery case is ideal. Battery power currently dominates the wearables market and offers the ability to co-locate a Bluetooth or equivalent far-field RF transmitter for convenient real-time wireless data readout. However, batteries, alongside the inductors used for dc-dc conversion, can occupy significant device volume, leading to devices that are not sufficiently miniaturized to fit comfortably on or within the human anatomy. Even when the volume of a device is dominated by batteries, users still often complain about poor battery life in their wearables, and as the number of devices worn increases, re-charging batteries on any regular interval may be prohibitive. Wireless power can eliminate the need for a battery integrated on the wearable itself, yet just pushes the need for a battery elsewhere— usually right on the top of the wearable, which does not ultimately save volume. While a mobile phone, which users are conditioned to charging daily anyways, could potentially be used as the wireless power source, this involves significant user frictions in terms of data acquisition—measurements are only collected when the phone is placed in close proximity to the wearable, moving data collection from continuous real-time readout to infrequent spot measurements initiated by an unreliable user.

To accommodate continuous data readout using a far-field radio without having to re-charge large batteries, energy harvesting can be employed. However, most sources of energy harvesting on the human body offer limited power densities (e.g., <30 µW/cm$^2$), and, importantly, are highly stochastic and cannot be relied on as the sole source of energy in the system. Furthermore, even when aggregating multiple harvesting sources to increase the probability of successful harvesting, most such systems still require a battery, and in any case, also require at least one large inductor for efficient variable dc-dc conversion.

One type of wearable energy harvesting device includes biofuel cells. Biofuel cells (BFCs), which are devices that convert biochemical energy into electrical energy via enzymatic electrochemical reactions, offer an intriguing energy harvesting solution for physiochemical sensing wearables. While the power generated by a BFC is stochastic, if properly conditioned, the generated power is also proportional to the underlying fuel concentration. Thus, a BFC energy harvester can also be simultaneously utilized as a self-powered physiochemical sensor.

In such a case, for example, only when the quantity to sense is present in fluid, will the BFC energy harvester operate and data readout will occur—there is no need for an energy-smoothing battery. BFCs harvesting energy from on-body lactate can offer high energy densities, e.g., as high as 1 mW/cm$^2$ in some implementation. Notably, this is more than sufficient to power electronic readout circuits with far-field radios. Also, interestingly, the open-circuit voltages of such BFCs are on the order of 0.3-0.5 V, which is just to the range where CMOS circuits can potentially operate. For example, a wireless temperature sensor can potentially operate directly from the output of a BFC without a dc-dc converter.

Disclosed are devices, systems and methods for performing sensing of metabolites while using the power from a biofuel (e.g., the metabolite) to directly power an analog-to-digital converter and wireless transmitter, without requiring any external power source.

In some embodiments in accordance with the disclosed technology, a wireless physiochemical sensing system capable of monitoring glucose or lactate when powered via an enzymatic biofuel cell (BFC) based on energy naturally present in the underlying analytes to be sensed. Unlike conventional BFC harvesters, which utilize bulky boost converters to increase the BFC voltage (e.g., 0.3-0.4V) to a higher level suitable for conventional CMOS circuits, the disclosed enzymatic biofuel cells implemented in accordance with the disclosed technology forgoes any DC-DC converter, and instead the entire system, e.g., including a delta-sigma modulation analog-to-digital converter (DSM ADC) and 920 MHz RF transmitter, is designed to operate directly from the dynamic 0.3-0.4V BFC output.

In some implementations, to avoid the need for a bulky dc-dc converter, the wireless sensing system is directly powered from the near-open-circuit voltage of the BFC, and the BFC is periodically duty-cycled to the maximum power point (MPP) to perform analyte concentration readout measurements. The example designs of a wireless physiochemical sensing system described herein demonstrate the capability of monitoring glucose or lactate, powered directly by a glucose or lactate BFC. Yet, it is understood that other analytes can also be used in accordance with the present technology. Example embodiments and example implementations of the disclosed systems, methods and devices are discussed in more detail, along with more detailed descriptions and analysis of how the example circuits were optimized for operation at low voltage (e.g., 0.3-0.4 V), alongside example measurement results demonstrating their achievement.

Enzymatic BFCs can produce electrical power from renewable biocatalytic enzymes and metabolytes (e.g., glucose and lactate) operating as fuels. The electrons harvested from such metabolytes can then be delivered into an electronic circuit as a source of power. Self-powered sensors based on BFCs hold an advantage to minimize interference effects from complex biofluids.

Yet, there are significant challenges to interfacing BFCs to electronics. For example, BFCs do not operate perfectly analogous to conventional energy harvesters such as photovoltaics (PVs) or thermoelectric generators (TEGs). Instead, BFCs can be thought of as a hybrid battery/energy harvester—while there is an MPP, continuously harvesting at the MPP will deplete the underlying fuel at the maximum possible rate. If there is a continuous replacement of this fuel, for example, during periods of high sweating, then this may not be a problem. However, in practical applications, it is difficult to guarantee that fuel replacement will occur at the same rate as energy extraction, and thus, operational longevity is not guaranteed. Thus, with BFCs, it is generally best to not always operate at the MPP, but rather, only operate at the minimum rate of energy extraction needed to continuously sustain the system.

FIG. 1A shows a diagram of an example embodiment of a DC-DC-converter-free biofuel cell-powered system architecture, in accordance with the present technology, which in some implementations includes a glucose/lactate biosensor system. As illustrated in the diagram, a BFC is modeled as a voltage source, $V_{BFC}$, with a series source resistance, $R_{BFC}$, creating an input voltage to the energy harvester, $V_{IN}$, of the example BFC-powered wireless system.

Figure 1B:
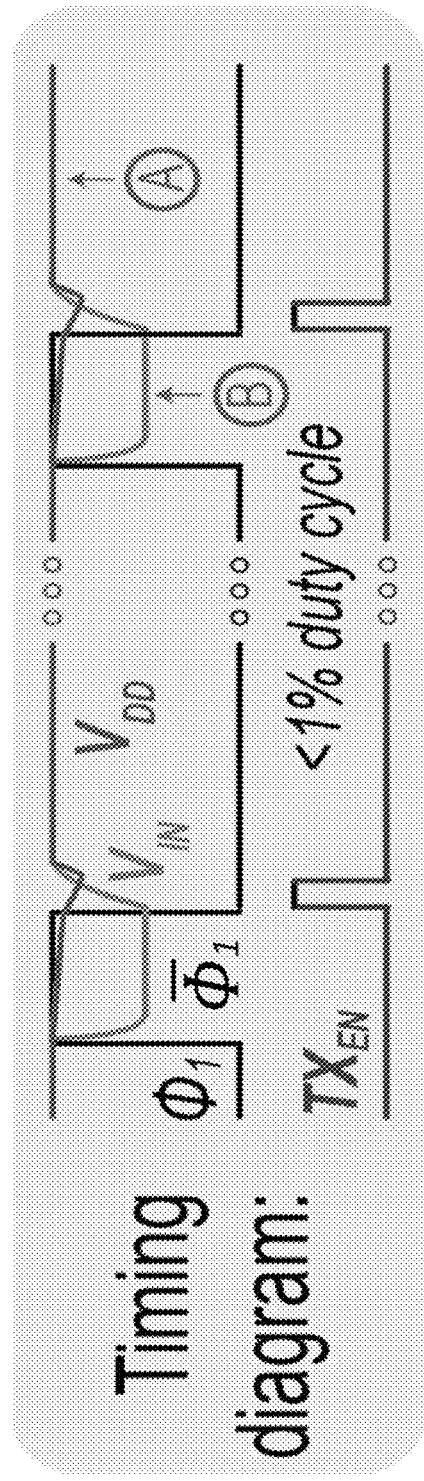
FIG. 1B shows a functional timing diagram for an example implementation of the system of FIG. 1B.
Figure 1C:
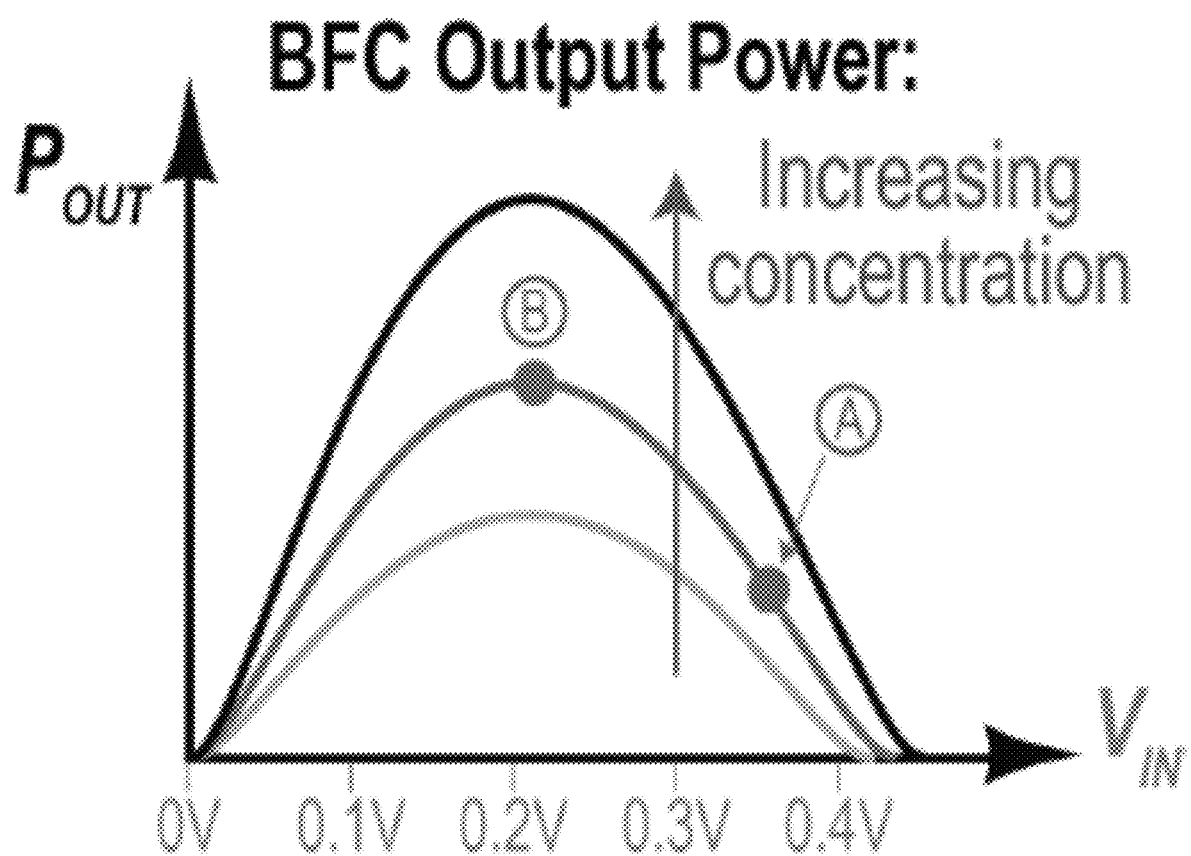
FIG. 1C shows a plot representative of example biofuel cell polarization curves.

FIG. 1C shows output power of an example biofuel cell versus input voltages, representative of BFC polarization curves. According to the example BFC model, the polarization curves of a typical BFC are represented in the data plot of FIG. 1C. For example, when attempting to power a high-current load, the BFC is overloaded and drops most of the voltage across $R_{BFC}$ and thus, $V_{IN}$ is low; when attempting to power a low-current load, very little voltage is dropped across $R_{BFC}$, and thus, $V_{IN}$ is approximately equal to $V_{BFC}$, or the BFC's open-circuit voltage (point A in FIG. 1C). In between these two extremes is the MPP, where, when the BFC is presented with a matched load, its output power is maximized (point B in FIG. 1C). As the fuel concentration increases, the output power at the MPP increases linearly. Outside of the MPP, the concentration to output power relationship is not necessarily linear. Thus, a self-powered biosensor should, during readout, operate at the MPP.

A self-powered BFC-based biosensing detection can be operated at the MPP at a low duty ratio, with the majority of the time spent operating in a lower-power mode [e.g., point A in FIG. 1C]. With the open-circuit voltage of BFCs is on the order of 0.3-0.5 V, the example system architecture is designed to forgo a dc-dc boost converter (and its bulky inductor), and instead directly power the system from $V_{IN}$.

Since a dc-dc converter is no longer used, a matched resistor can be periodically deployed for MPPT purposes.

The overall system architecture is shown in FIG. 1A. As shown in FIG. 1A, at steady state, the BFC passes current through switch S1 during phase $\Phi_1$ to establish $V_{DD}$, which is near the open circuit voltage of the BFC, as the circuit is in a low-power sleep state for the majority of phase $\Phi_1$. During the phase $\Phi_1$, switch S1 is closed and switch S2 is open. Since continuously presenting a matched load at the MPP depletes fuel at the maximum possible rate, limiting operational longevity, the system instead only presents a matched load, $R_{MPP}$, at a 1% duty ratio via periodic activation of switch S2 during phase $\overline{\Phi}_1$. During the phase $\overline{\Phi}_1$, switch S1 is open and switch S2 is closed.

During phase $\overline{\Phi}_1$, the system is sustained by a 1 µF 1×0.5 mm² ceramic decoupling capacitor, $C_{DD}$. The matched resistor, $R_{MPP}$, is implemented on-chip as a 3-bit binary weighted resistance, with resistance ranging, for example, from 30 to 200Ω. During phase $\overline{\Phi}_1$, a passive $\Delta\Sigma$ analog-to-digital converter (ADC) samples and digitizes $V_{IN}$, which drops according to the MPP and applied resistance, to compute the MPP, and therefore infer analyte concentration. Digitized data are then serialized, buffered, and delivered to an integrated wireless transmitter.

FIG. 1B shows functional timing diagram of an operation of the example system of FIG. 1A. The example timing diagram represents the voltage across the decoupling capacitor ($V_{DD}$) and BFC terminal ($V_{IN}$) while the BFC is periodically duty-cycled to the maximum power point (MPP) at a rate of %1. In phase $\Phi_1$, the BFC terminal ($V_{IN}$) is directly connected to the system ($V_{DD}$), and the BFC is operating in a lower power mode. This lower power mode is equivalent to a voltage close to the open circuit potential which is shown as point A, also shown as point A in FIG. 1C. During phase $\overline{\Phi}_1$, in which the system is sustained by $C_{DD}$, the matched resistor, $R_{MPP}$, is connected to the BFC terminal and therefore, $V_{IN}$ drops to the maximum point voltage, shown as point B, also shown as point B in FIG. 1C. During this phase, a passive $\Delta\Sigma$ modulator samples and digitizes $V_{IN}$. This timing diagram also shows that, in this example, the power oscillator-based transmitter, which wirelessly transmits the sensed data, is deeply duty-cycled (<1%) and activated once every 14.3 ms.

Figure 1D:
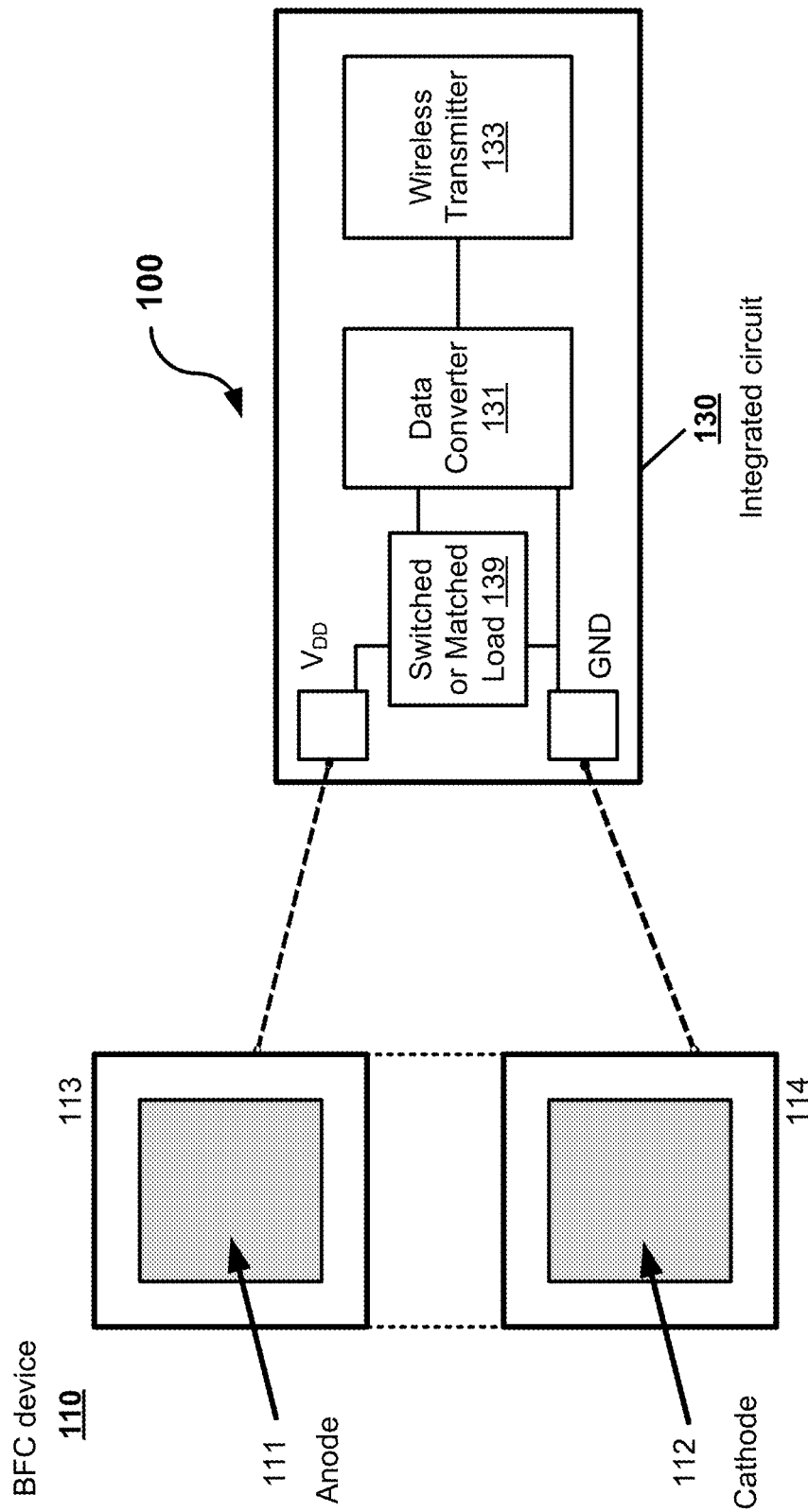
FIG. 1D shows a diagram illustrating an example embodiment of a biofuel cell powered electronic circuit in accordance with the present technology.

FIG. 1D shows a diagram illustrating an example embodiment of a biofuel cell powered electronic circuit 100, which is self-powered by a biofuel (e.g., glucose or lactate) and modulated at a low voltage to power an integrated circuit connected to the biofuel cell contingent. The BFC-powered electronic circuit 100 includes one or more integrated circuits 130, also referred to as an electronic circuit 130, coupled to a biofuel cell device 110. The biofuel cell device 110 includes an anode 111 including a conductive electrode that is coupled to a substrate 113, where an enzymatic layer is formed on the conductive electrode of the anode 111 and configured to electrochemically interact with the biofuel (e.g., glucose or lactate) in a fluid. The anode 111 is electrically coupled to a power supply voltage terminal (e.g., $V_{DD}$) of the electronic circuit 130. The biofuel cell device 110 includes a cathode 112 including a conductive electrode, e.g., which can include a nanocomposite, that is coupled to a substrate 114. The cathode 112 is electrically coupled to a ground voltage terminal (e.g., GND) of the electronic circuit 130. In some embodiments, the substrate 113 and the substrate 114 is a single substrate, where the anode 111 and the cathode 112 are spaced apart on the single substrate. The $V_{DD}$ of the electronic circuit 130 is set to a voltage of 0.25 V to 0.6 V (e.g., 0.3 V to 0.4 V in some implementations), which is near the open circuit voltage of the BFC device 110. The electronic circuit 130 includes a data converter 131 to translate the power generated by the biofuel cell device 110 to a transmittable data. For example, in some embodiments, the data converter 131 includes a delta-sigma modulation analog-to-digital (DSM ADC) converter or a ring oscillator, which is able to operate directly from the power generated by the enzymatic layer to use a maximum power point of the enzymatic BFC device 110 to infer the biofuel concentration in the fluid. In this manner, for example, the electronic circuit 130 is operable to translate the electrical energy as transmittable digital data that is indicative of a concentration of the analyte (e.g., biofuel) in the fluid. To control the operation of the data converter 131, for example, the electronic circuit 130 includes a switched or matched load 139 coupled between the anode 111 and the data converter 131 to control supply of the electrical energy (e.g., electrical current) extracted from the biofuel to the electronic circuit 130. For example, the switched or matched load 139 can connect the anode 111 of the biofuel cell device 110 to the data converter 131, in some implementations, to establish a supply voltage at a maximum power point in a range, e.g., of 0.25 V to 0.6 V (in some examples, to the maximum power point that can include a range of 0.3 V to 0.4 V). Also, for example, in some implementations where embodiments of the data converter 131 include the ring oscillator, the switched or matched load 139 can connect the anode 111 to the ring oscillator to establish a supply voltage that is set by a fixed load.

In implementations of the BFC-powered electronic circuit 100, for example, the electronic circuit 130 is configured to use power generated while the biofuel (e.g., glucose or lactate) is being decomposed by the enzymatic layer of the anode 111 while also determining information about the biofuel (e.g., concentration of the biofuel in the fluid), thereby functioning as a self-powered biosensing system and bioelectronic system that can be employed in a variety of bio-related applications. In some embodiments, the electronic circuit 130 can include a wireless transmitter 133 in electrical communication to the data converter 131, which can transmit the converted digital signals as data.

In some example embodiments, the electronic circuit 130 can include analog signal conditioning circuitry, an analog-to-digital converter, or a wireless transmitter, or a combination of any two or more of the analog signal conditioning circuitry, the analog-to-digital converter, and the wireless transmitter.

In some example embodiments, the enzymatic layer includes lactate or glucose oxidase (LOx or GOx). In some example embodiments, the enzymatic layer can also include bovine serum albumin (BSA). In some example embodiments, the anode 111 includes a carbon nanotube (CNT)-based mediator nanocomposite formed on a thin layer of carbon. In some example embodiments, the cathode 112 includes a carboxylated-CNT/Ag$_2$O nanocomposite. A diagram of this example embodiment is shown later in FIG. 12B.

Example ADC Architecture

Since the energy available from the glucose/lactate BFC harvester is limited and its open-circuit voltage is very low (e.g., 0.3-0.5 V), the target analog-to-digital converter (ADC) should operate under as low as 0.3 V and consume ultra-low power. Among various ADC architectures, the successive approximation register (SAR) ADC has been demonstrated to be highly efficient and its $V_{DD}$ can readily be scaled down to very low voltages as it mostly includes digital circuits. Compared to oversampled delta-sigma ADCs, the SAR ADCs are op-amp-free architecture, and thus, do not require high-gain and high-bandwidth op-amps, which consume significant static power.

However, the achievable effective number of bit (ENOB) in SAR ADCs is low (e.g., 8-9 bits). To increase ENOB beyond 10 bits, digital-to-analog converter (DAC) calibration technique, noise-shaping architectures, or data driven noise-reduction methods are required to overcome DAC capacitive array mismatch and comparator noise, which demand exponentially growing capacitive DAC size, circuit overhead, and large power. Thus, SAR ADCs are not necessarily the best choice for this application.

In turn, $\Delta\Sigma$ ADCs exploit oversampling and noise-shaping advantages to reduce noise. However, $\Delta\Sigma$ ADCs largely depend on power-expensive op-amps, and thus, traditional $\Delta\Sigma$ modulator ($\Delta\Sigma M$) circuits are not practical at 0.3 V. Inverter-based $\Delta\Sigma$ Ms and bulk-driven techniques are among possible ultra-low-voltage $\Delta\Sigma M$ designs. Yet, the power consumption constraint can limit their use in self-powered applications.

Since designing amplifiers to attain low noise and large gain at low supply voltages is difficult without consuming microwatts of power, an energy-efficient passive discrete time (DT) $\Delta\Sigma M$ is employed here. Unlike the active integrator shown in FIG. 2A, the passive integrator, depicted in FIG. 2B, draws no direct current from $V_{DD}$, therefore reducing the $\Delta\Sigma M$ power. Also, $V_{DD}$ can readily be scaled down to 0.3 V, assuming the gate of switching transistors is adequately driven.

Figure 2A:
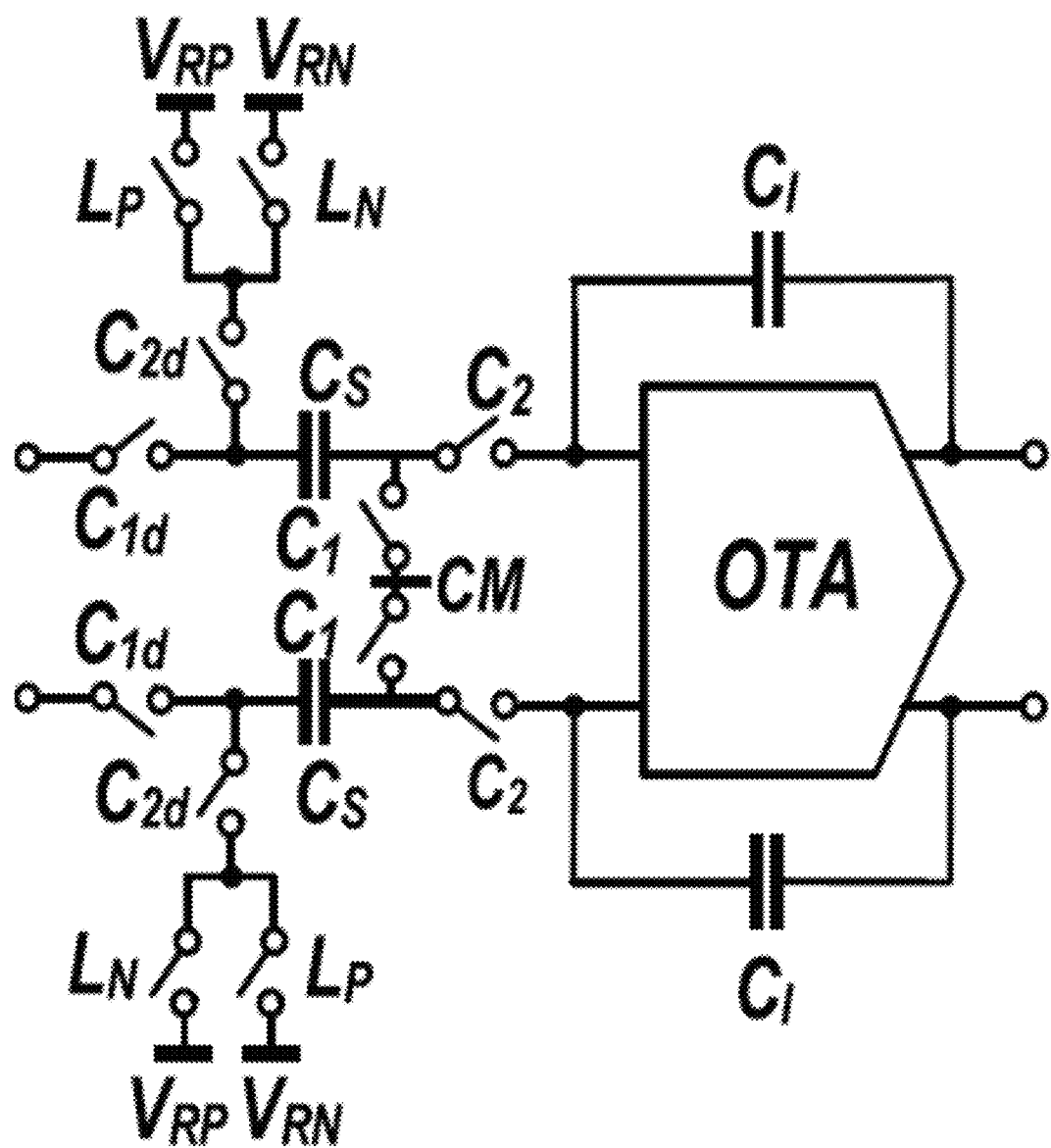
FIG. 2A shows a circuit diagram of an example embodiment of an active integrator using power-consuming operational transconductance amplifier (OTA).
Figure 2B:
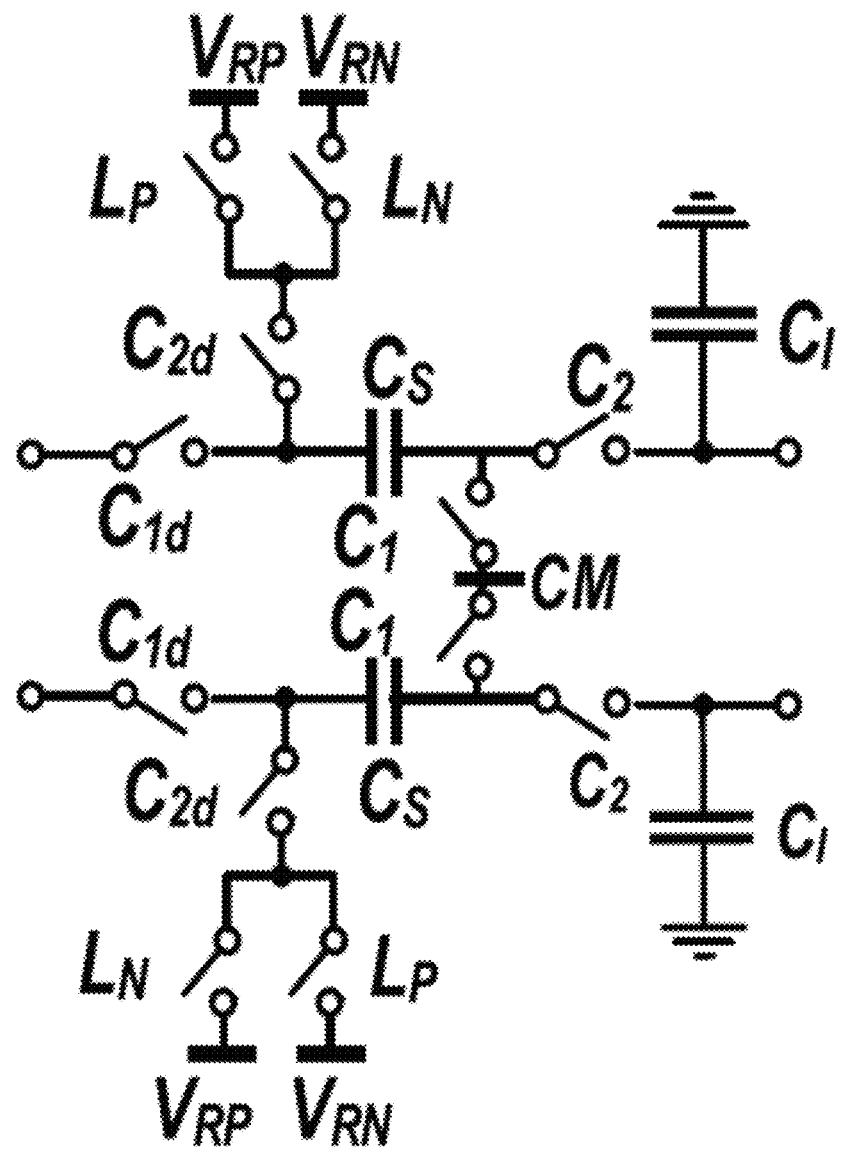
FIG. 2B shows a circuit diagram of an example embodiment of a power-efficient passive integrator.

FIGS. 2A and 2B show circuit diagrams of an example embodiment of an active integrator using power-consuming operational transconductance amplifier (OTA) and a power-efficient passive integrator, respectively.

Utilizing a charge pump to increase system $V_{DD}$ to more robustly operate an op-amp would require even more power than the low-voltage designs and would also introduce additional inefficiencies in the charge pump itself, which is generally limited to ~85% efficiency using on-chip capacitors. For example, the passive integrator has several advantages over its active counterpart: it is 1/f-noise free, critical for low signal bandwidths, and more linear. The operational transconductance amplifier (OTA) of the active integrator operating from a 0.3-V $V_{DD}$ suffers from low-voltage headroom, and thus, suffers from nonlinearity. However, the passive integrator approach does have several shortcomings: with the same oversampling ratio (OSR), a passive modulator requires larger capacitors to maintain the same thermal noise level and lowpass filtering corner frequency as an active integrator. Also, passive integrators suffer from lack of dc gain—they are known as leaky integrators—which makes the modulator more prone to coupling noise, and thus, its signal-to-noise ratio (SNR) is typically lower than the standard active $\Delta\Sigma M$. Here, low SNR is traded for lower power consumption at low voltage in this application.

Example $\Delta\Sigma$ ADC Model

Figure 3A:
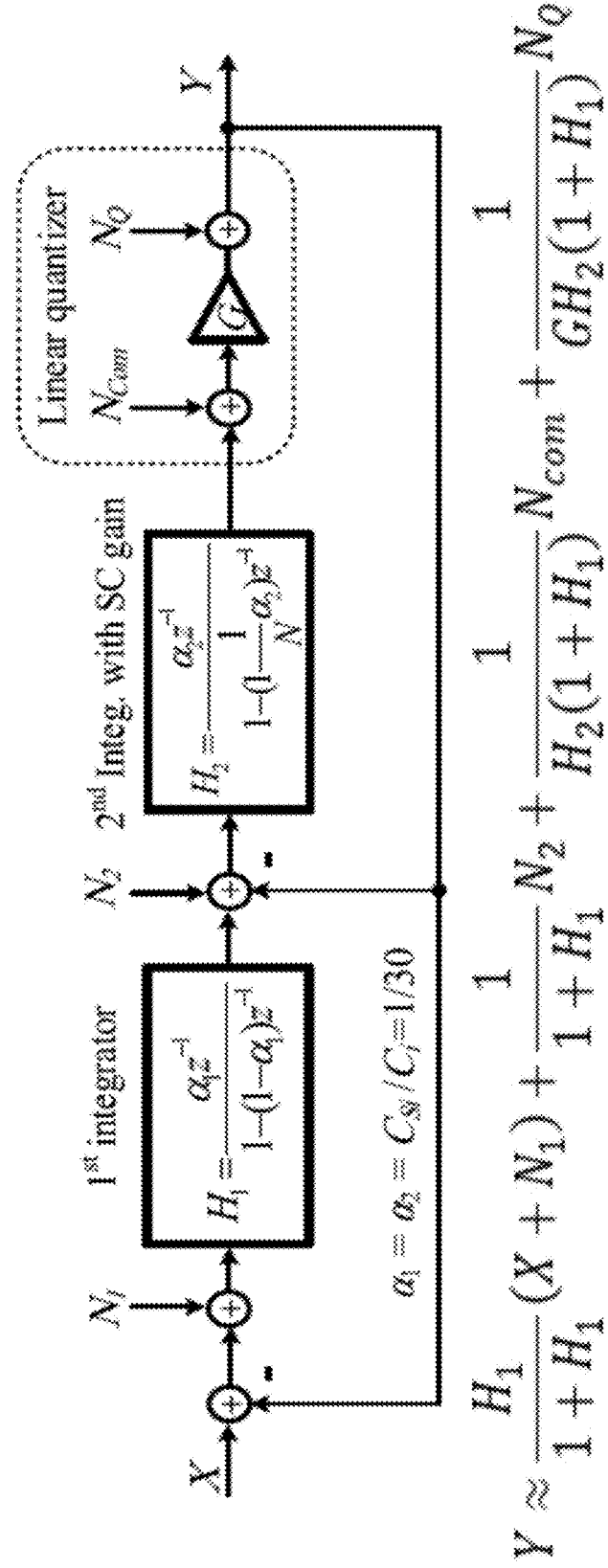
FIG. 3A shows a block diagram of an example embodiment of a 2nd-order passive 1-bit discrete-time delta sigma modulator (DT ΔΣM) using passive filters in accordance with the disclosed technology.

FIG. 3A shows the simplified linear model of a 2nd-order single-loop 1-bit passive $\Delta\Sigma M$ used to sample the voltage across BFC terminal. The linearized model incorporates input-referred thermal noise of the passive integrators (i.e., $N_1$ and $N_2$), the preamplifier (i.e., $N_{Com}$), and the quantization noise (i.e., NQ). $\alpha_1$ and $\alpha_2$ represent the integrator's capacitor ratios, while N=5 denotes the switched capacitor (SC) passive gain in the 2nd integrator, which is realized by a gain-boosting scheme. In the model, G represents the total quantizer gain.

Figure 3B:
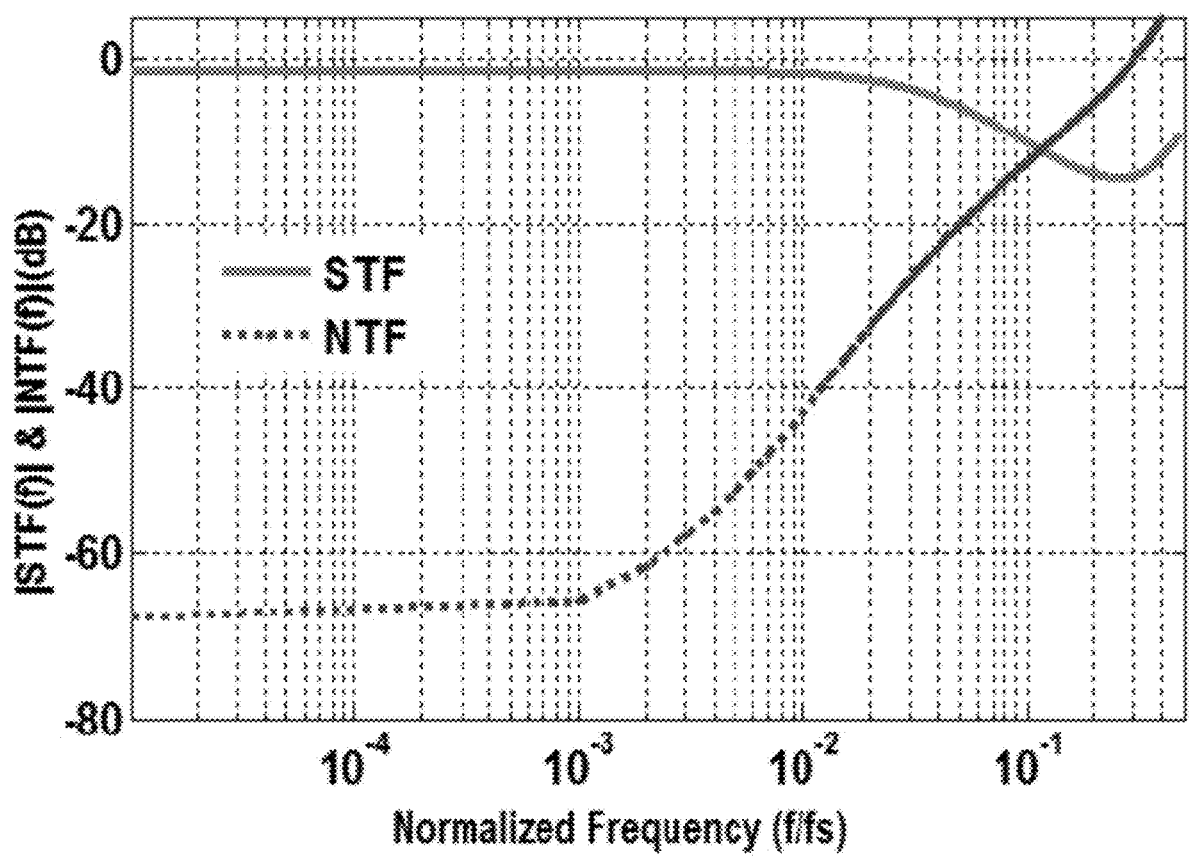
FIG. 3B shows a plot depicting a magnitude of signal transfer function (STF) and noise transfer function (NTF) of the example modulator.

FIG. 3B shows a data plot depicting the magnitude of signal transfer function (STF) and noise transfer function (NTF) of the example modulator. The NTF can be seen as the noise attenuation at the quantizer input.

Figure 3C:
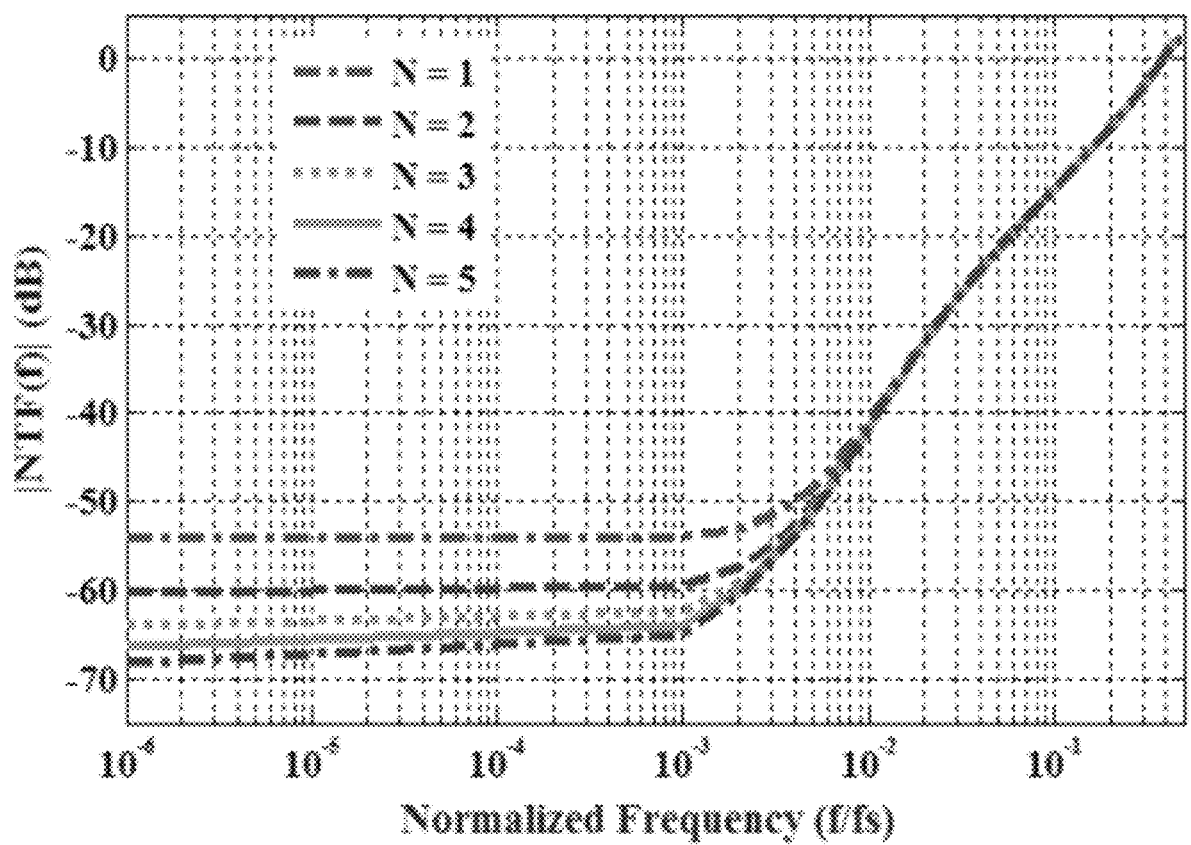
FIG. 3C shows a plot depicting a noise transfer function (NTF) magnitude for various values of passive gain, N.

FIG. 3C shows a data plot depicting NTF magnitude for various values of passive gain, N. Example simulation results in FIG. 3C show that the in-band noise reduces with increasing passive gain, N. However, N>5 is problematic since gain improvements saturate due to sampling capacitor parasitics, and hence, N=5 was chosen in this design.

Figure 3D:
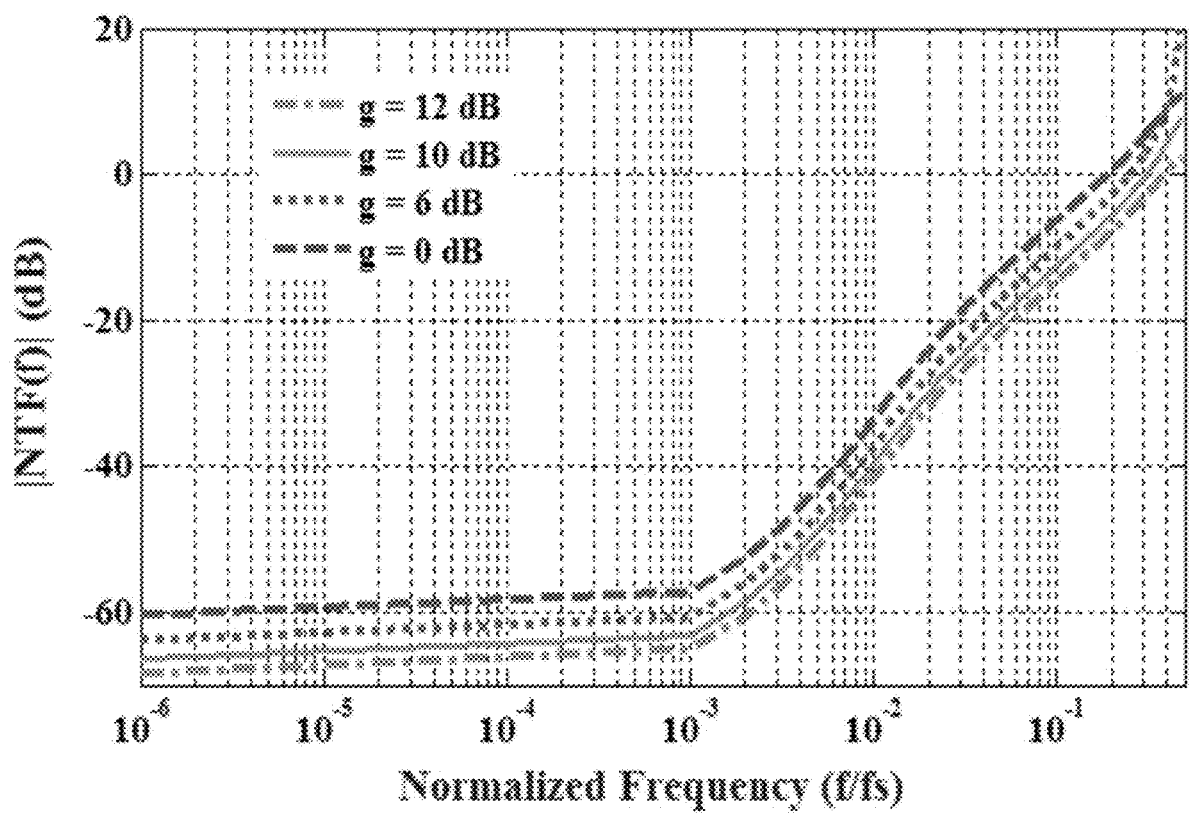
FIG. 3D shows effect of preamplifier gain g on the magnitude of NTF.

FIG. 3D shows a data plot depicting example behavioral simulation results showing the effect of preamplifier gain, g, on the magnitude of the NTF. The loop-gain necessary to process quantization noise-shaping in the passive modulator architecture, the term $NQ/GH_2(1+H_1)$ illustrated in FIG. 3A, comes mainly from the dc gain of the quantizer (including preamp).

Example $\Delta\Sigma$ ADC Circuit Design

Figure 4:
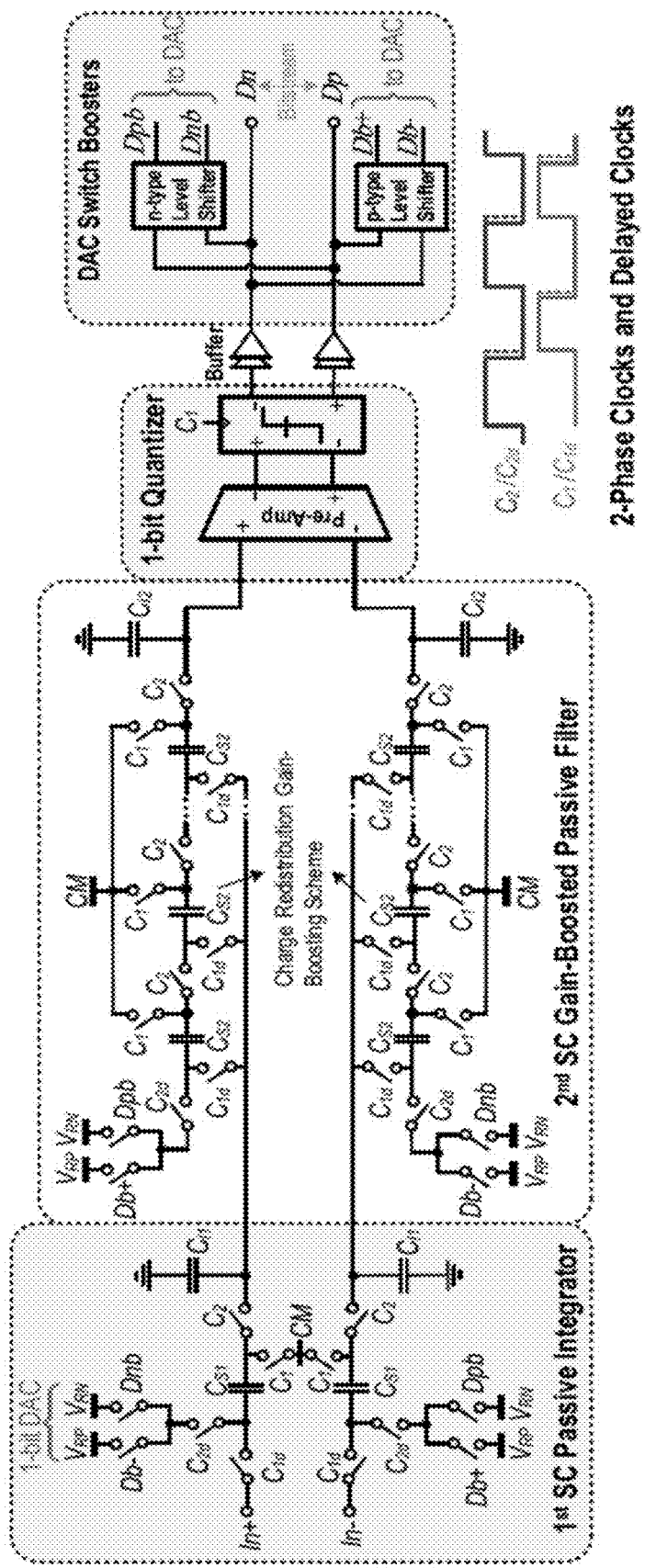
FIG. 4 shows a circuit schematic of an example 2nd-order passive 1-bit DT ΔΣ modulator in accordance with the disclosed technology.

FIG. 4 shows a circuit diagram illustrating an example $\Delta\Sigma M$ circuit embodiment, which utilizes a basic passive integrator in the 1st stage and a gain-boosting passive integrator in the 2nd stage, as an alternative to power hungry active integrators. The gain boosting scheme can potentially be used at the 1st stage to achieve a higher SNR, but due to nonlinear OFF currents of parallel sampling switches, the modulator signal to noise and distortion ratio (SNDR) degrades significantly.

For example, due to the internal signal attenuation at the 1st stage output, the 2nd stage has relaxed linearity requirement, and therefore utilizes a gain-boosting integrator to reduce in-band noise with minimal power penalty. Specifically, a charge redistribution scheme was employed, where the 1st integrator's output is sampled onto capacitors $C_{S2}$ in phase $C_1$ (all in parallel), and then, the pre-charged $C_{S2}$s are positioned in series to charge share with the integrating capacitor $C_{12}$ in phase $C_2$.

Taking advantage of low bandwidth voltage/current content of glucose/lactate BFCs, for example, $\Delta\Sigma M$ can use a relatively large OSR, which reduces in-band kT/C noise of the switching transistors, thereby decreasing capacitor size and the chip area. In some examples, the sampling and integrating capacitor sizes are 1 and 32 pF, respectively. The latter is determined from the filter −3-dB bandwidth, while the former is determined from the kT/C noise requirement.

At 0.3-V supply, it is very challenging to realize a good sampling switch due to significant degradation of the ratio of ON conductance and OFF current even when using low-$V_{th}$ transistors. The sampling switch needs a sufficiently high ON conductance to minimize nonlinear distortions, and the leakage current (OFF current) should be very low such that it does not result in signal-dependent ADC errors. To increase the ratio of ON conductance and OFF current, numerous circuit techniques were employed in the sampling switch.

Figure 5A:
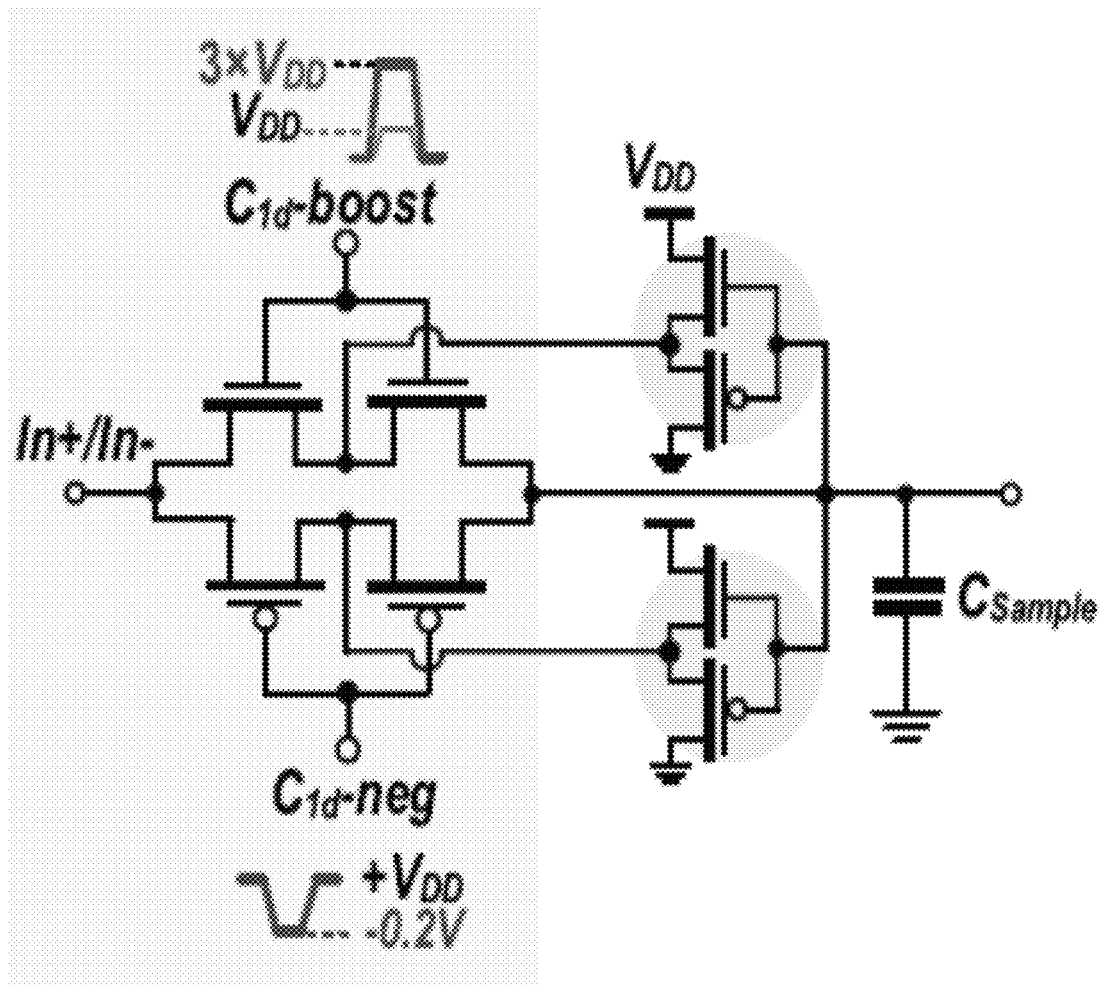
FIG. 5A shows a diagram of an example sampling switch with improved ON conductance.
Figure 5B:
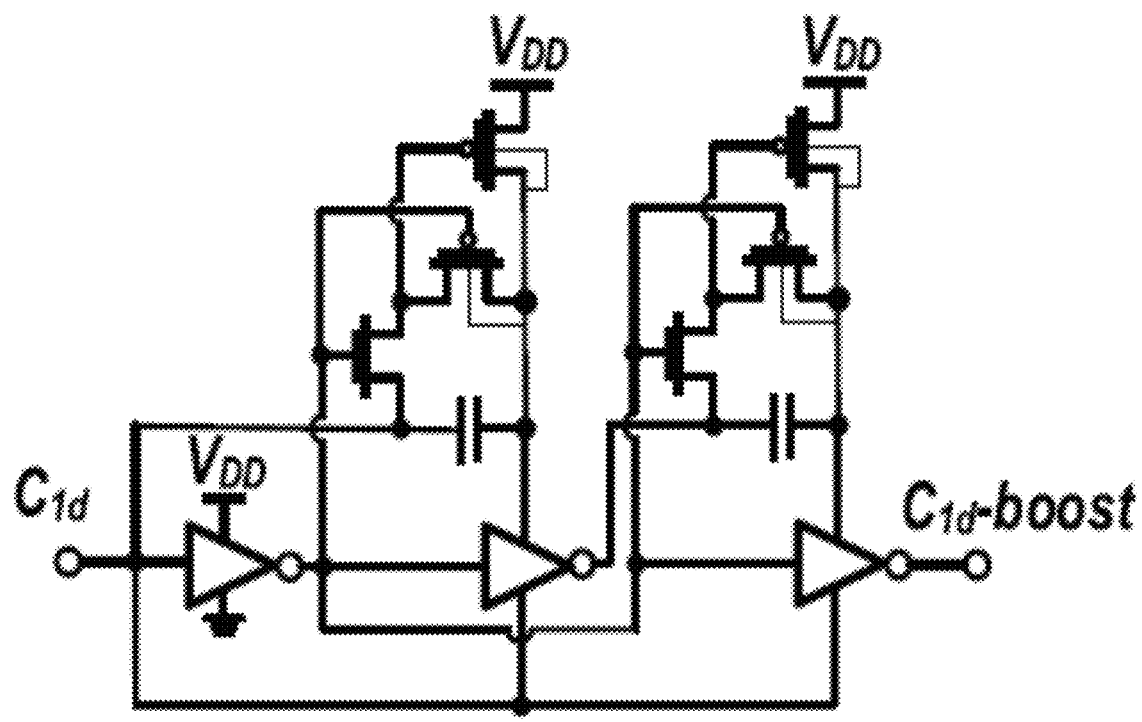
FIG. 5B shows a circuit diagram of an example 3× clock booster for driving a gate of an n-switch.
Figure 5C:
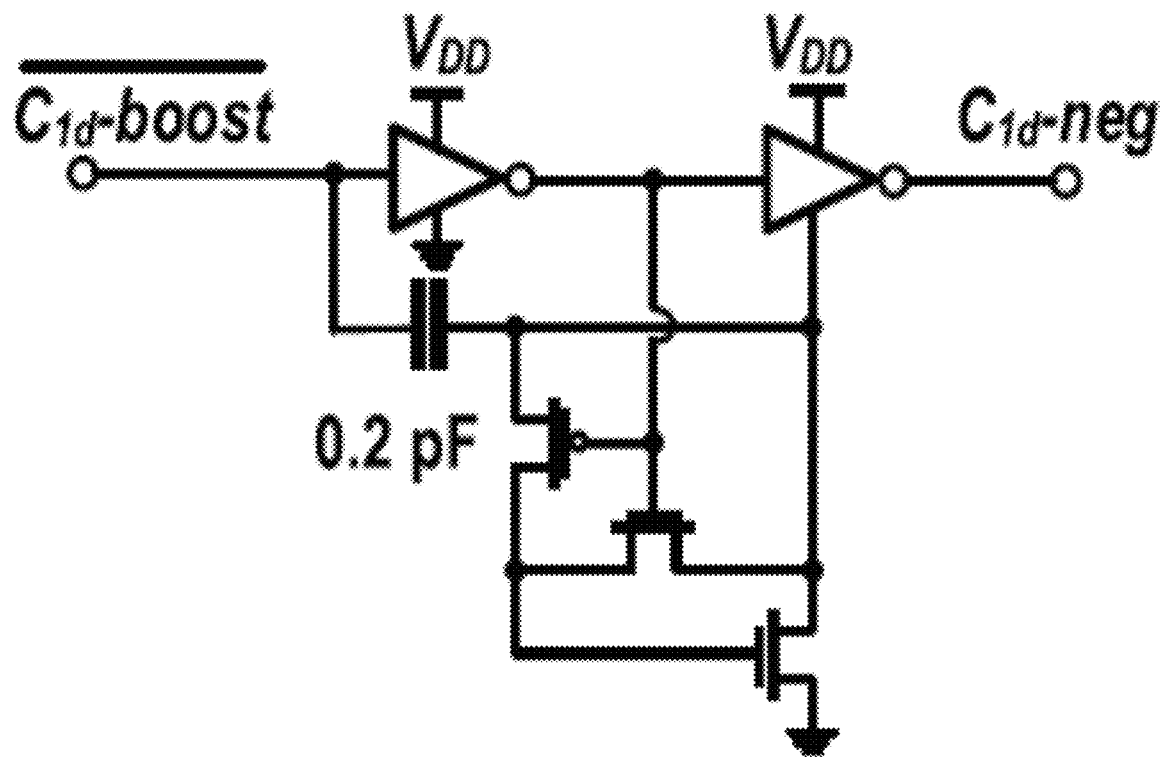
FIG. 5C shows a circuit diagram of an example negative level shifter for driving a gate of a p-switch.

FIG. 5A shows a diagram of an example sampling switch with improved ON conductance. FIG. 5B shows a circuit diagram of an example 3× clock booster for driving a gate of an n-switch. FIG. 5C shows a circuit diagram of an example negative level shifter for driving a gate of a p-switch.

As shown in FIG. 5A, the gate of NMOS transistors is driven by a 3× voltage boosting circuit depicted in FIG. 5B that improves ION/IOFF by 92%, and the gate of PMOS transistors is activated by a negative clock level shifter shown in FIG. 5C.

For example, using the example p-type level shifter circuit brings the PMOS gate voltage down to a −200 mV, resulting in an 8-dB SNDR improvement. Meanwhile, cascaded transmission gates help reduce OFF current, and the employed OFF-current-limiting feedback amplifier including a PMOS source follower and a leakage-current-biased NMOS further decreases the switch nonlinear leakage current, simply by pushing the internal nodes to the same voltage as the sampling capacitors (FIG. 5A), and thus reducing $V_{ds}$ and $I_{ds}$, respectively.

The other switches in example ΔΣ M shown in FIG. 4 are designed, for example, using NMOS or PMOS transistors and are activated by a 3× clock booster (for NMOS), or a −200-mV charge pump (for PMOS), as shown in FIGS. 5B and 5C.

Figure 6A:
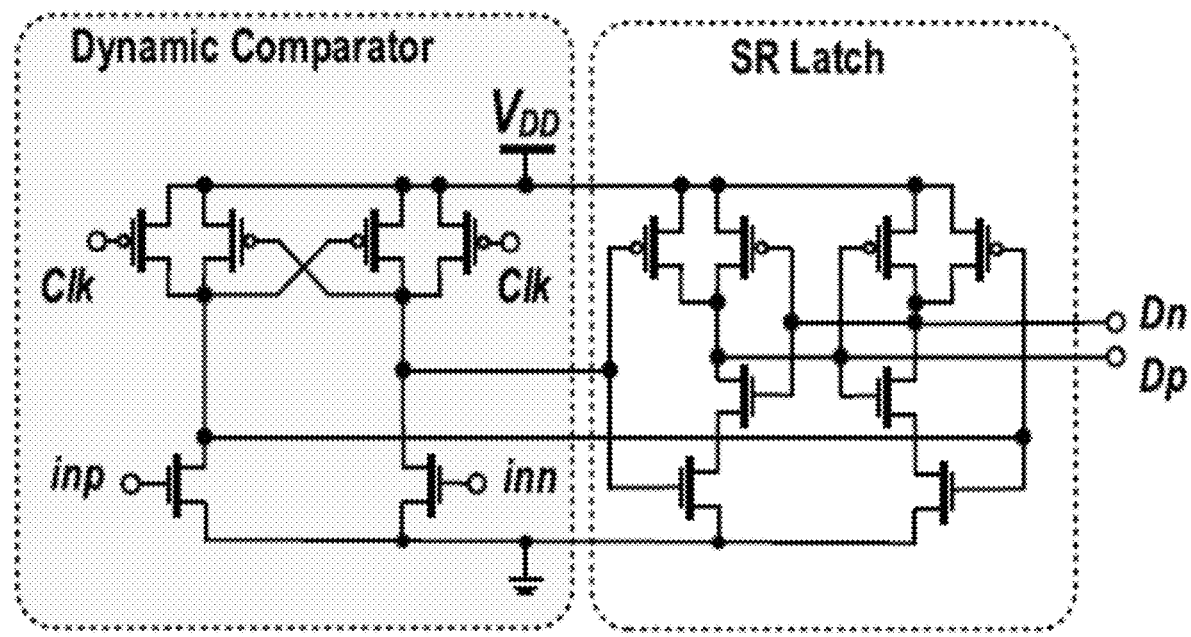
FIG. 6A shows a diagram of an example subthreshold dynamic comparator.
Figure 6B:
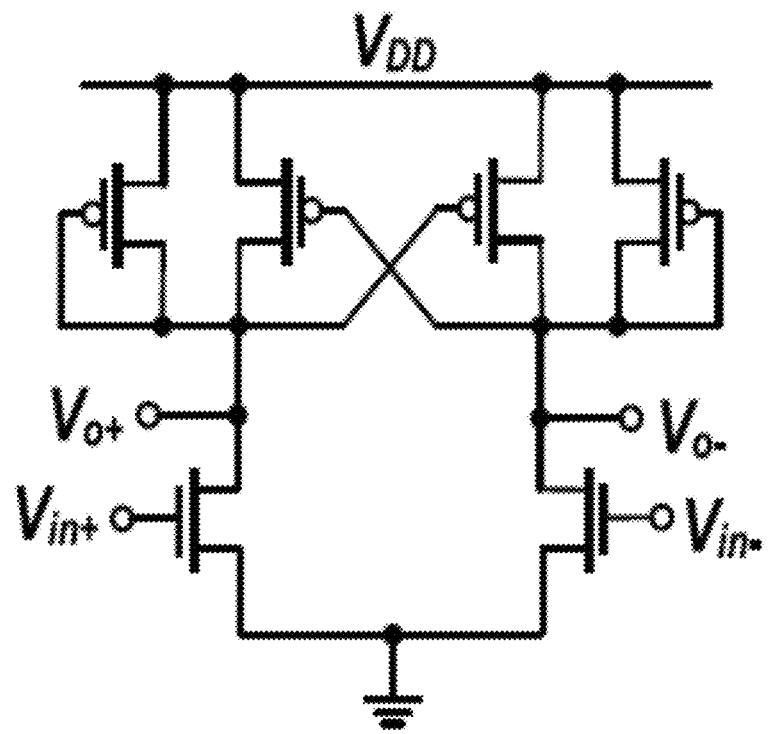
FIG. 6B shows a diagram of an example subthreshold preamplifier circuit.

FIGS. 6A and 6B show diagrams of example embodiments of a subthreshold dynamic comparator (FIG. 6A) and a subthreshold preamplifier circuit (FIG. 6B). The 1-bit quantizer is realized via a dynamic comparator followed by an SR latch, as shown in FIG. 6A. To mitigate comparator nonidealities (e.g., kick-back noise and offset) and relax comparator sensitivity, a preamplifier circuit is employed, as shown in FIG. 6B.

For robust operation at 0.3 V in the subthreshold regime, low-threshold transistors are used and only two transistors are stacked to mitigate the low-voltage headroom. To boost the gain up to 25 dB without consuming significant power, for example, a cross-coupled load was employed, while diode-connected PMOSs maintain the output common-mode voltage at the supply mid-level.

Figure 7:
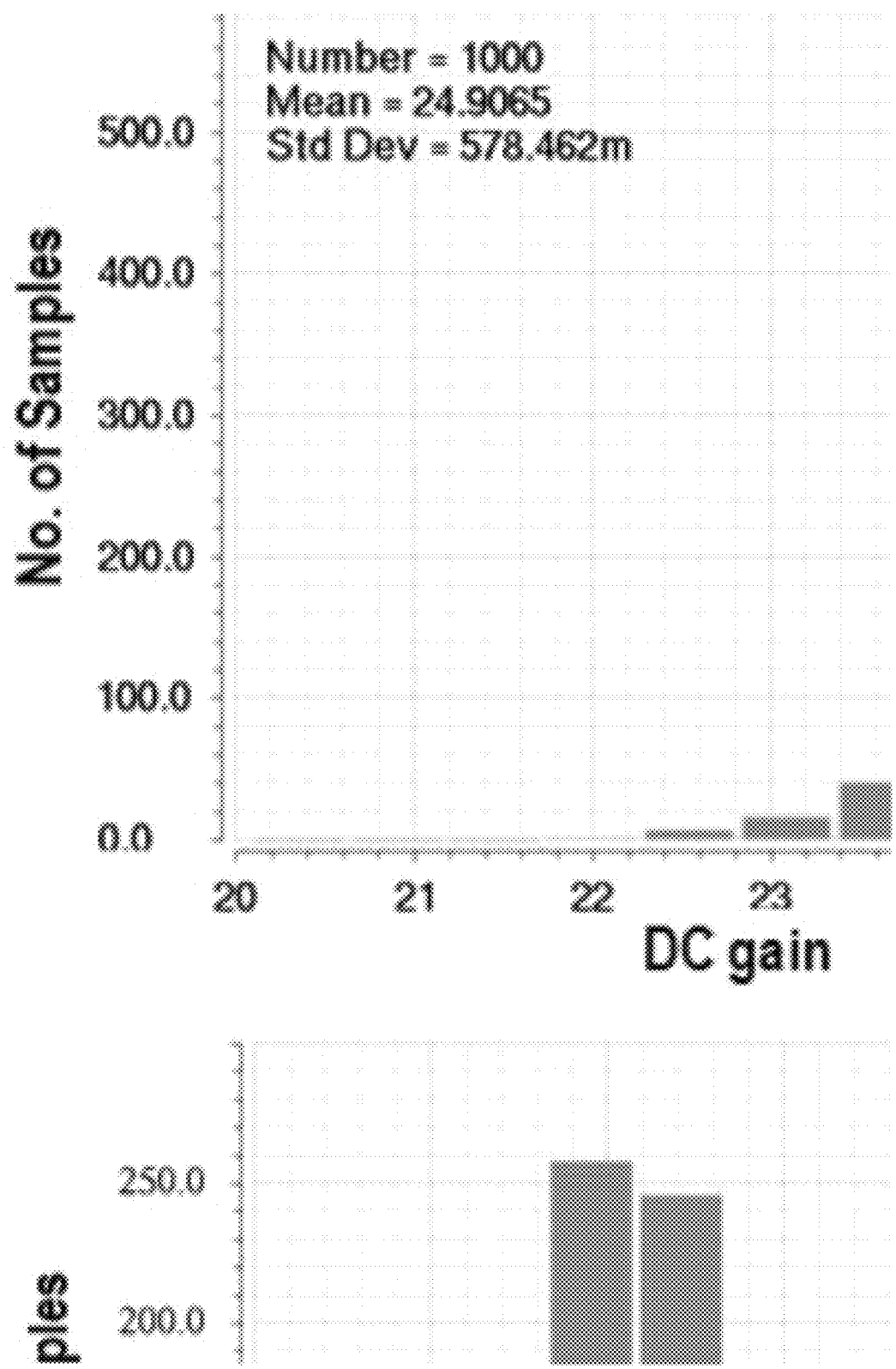
FIG. 7 shows a data plots depicting example Monte Carlo mismatch and process variation simulation results (1000 runs) for preamp DC gain and unity gain-bandwidth (GBW).

FIG. 7 shows a data plots depicting example Monte Carlo mismatch and process variation simulation results (e.g., 1000 runs) for preamp DC gain and unity gain-bandwidth (GBW). The Monte Carlo mismatch and process variation simulation results for preamp dc gain and unity gain-bandwidth (GBW) shown in FIG. 7, for example, demonstrate a mean value of 25 dB and 1.2 MHz for dc gain and GBW, respectively. The range of variations is acceptable for ΔΣ M design to meet the desired performance.

Figures 8A, 8B, 8C:
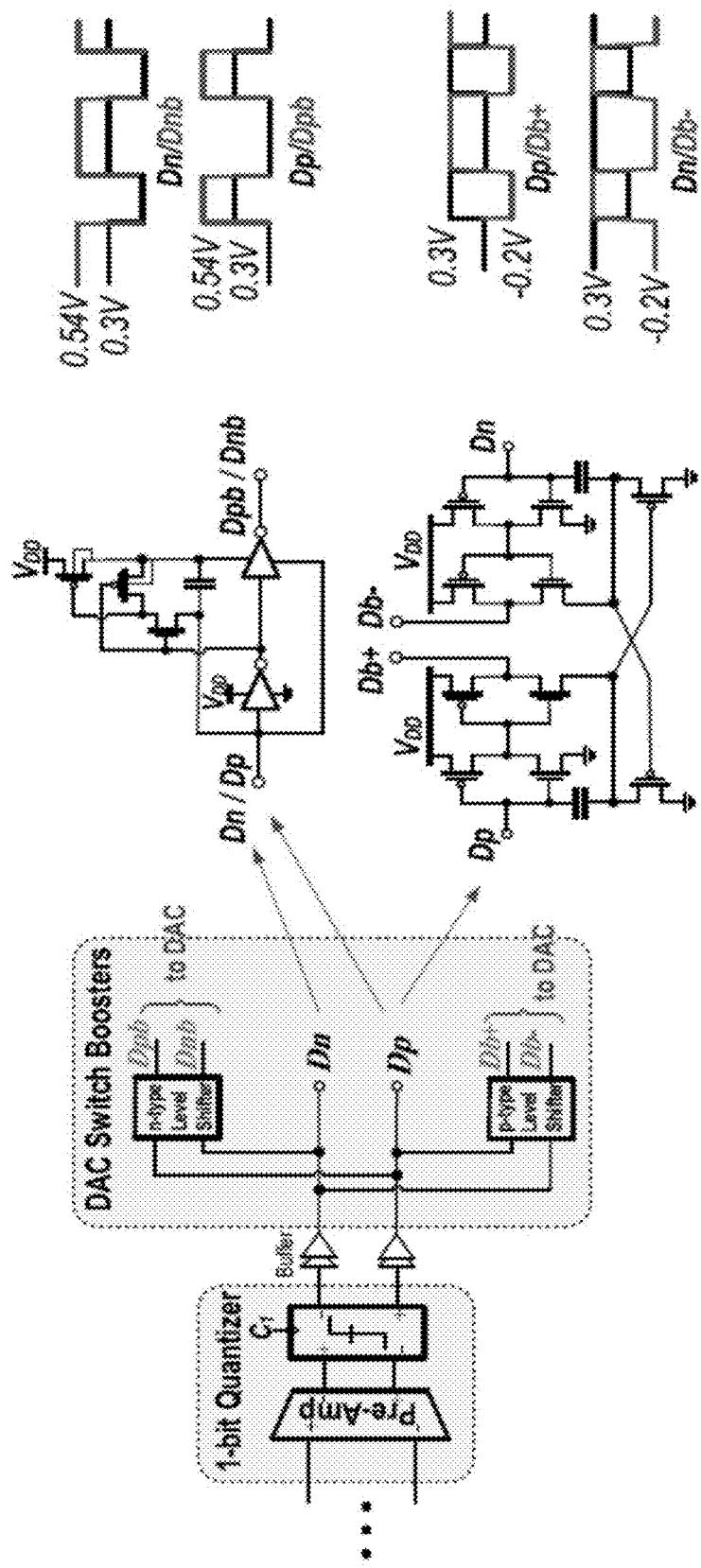
FIG. 8A shows a top-level block diagram of an example embodiment of a digital-to-analog converter (DAC) switch voltage boosters in accordance with the disclosed technology.
FIG. 8B shows a circuit schematic of an example 2× voltage booster for n-switch (top) and negative level shifter for p-switch (bottom) in accordance with the disclosed technology.
FIG. 8C shows a diagram depicting input and output waveforms of an example DAC switch voltage booster.

FIG. 8A shows a top-level block diagram of an example embodiment of a digital-to-analog converter (DAC) switch voltage boosters in accordance with the disclosed technology. FIG. 8B shows a circuit schematic of an example 2× voltage booster for n-switch (top) and negative level shifter for p-switch (bottom) in accordance with the disclosed technology. FIG. 8C shows a diagram depicting input and output waveforms of an example DAC switch voltage booster.

The example single-bit DAC is realized by using basic NMOS or PMOS switches connected to reference voltages VRP and VRN (FIG. 4). At 0.3-V supply, even when using low-$V_{th}$ transistors, it is not possible to turn on the DAC switches sufficiently. The output digital bits (Dn and Dp) of the single-bit quantizer (FIG. 8A) are thus buffered and level shifted by the n-type and p-type voltage level shifters to drive the gate of switches. The gate of NMOS switch is activated by a 2× clock booster, and the gate of PMOS switch is driven by a −200-mV charge pump circuit, as shown in FIGS. 8B and 8C.

As shown in FIG. 1A, the ADC samples the BFC data in phase $\overline{\Phi}_1$. However, during phase $\Phi_1$, the ΔΣ M's clocks are gated, and large, low-dropout NMOS switch placed between input transistors and ground of the preamp and comparator circuits separate them from $V_{DD}$ to save system power. The clock signals for ΔΣM (e.g., 256 kHz), Sinc² decimating filter (e.g., 1 kHz), Serializer (e.g., 10 kHz), and the TX (e.g., 1.024 MHz) are all generated from a 1.024 MHz master clock, generated either from an integrated ring oscillator or from an off-chip source. The 1.024 MHz clock is divided by 4 digitally to create a 256 kHz signal for ΔΣM, and it is used as a reference to generate two non-overlapping clocks ($C_1$ and $C_2$) and delays ($C_{1d}$ and $C_{2d}$) to eliminate charge injection between sampling and integrating phases of the ΔΣM. These four internal clock signals are buffered and then boosted 3× by the clock booster circuit shown in FIG. 5B. The clock signal $C_1$ (e.g., 256 kHz) is divided by 256 using an 8-bit counter to obtain a 1 kHz clock for use in Sinc² decimation filter.

Figure 9A:
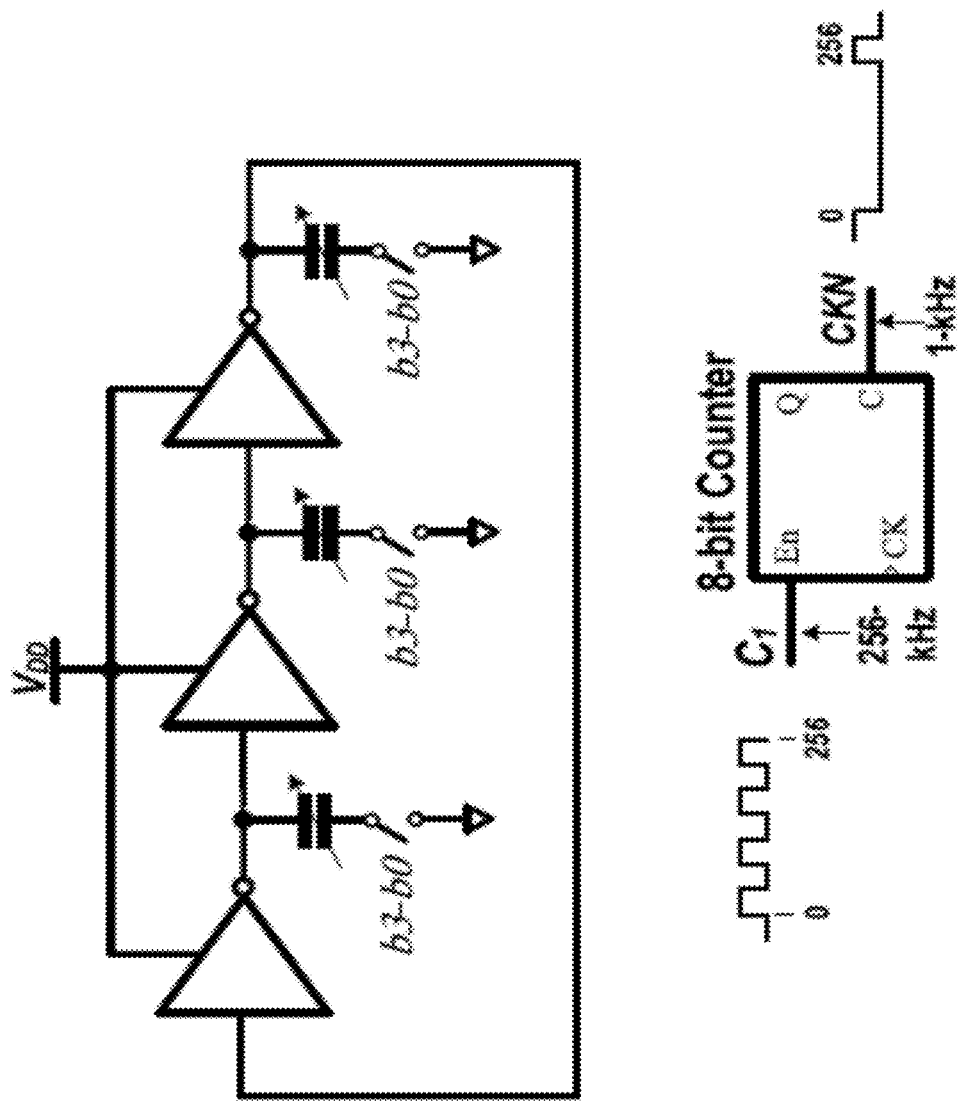
FIGS. 9A and 9B show diagrams depicting clock generation circuits including a 1.024-MHz ring oscillator and an 8-bit counter used to generate a 1-kHz signal from the sampling clock C1 (FIG. 9A) and a non-overlapping clock generator followed by clock boosting (FIG. 9B).
Figure 9B:
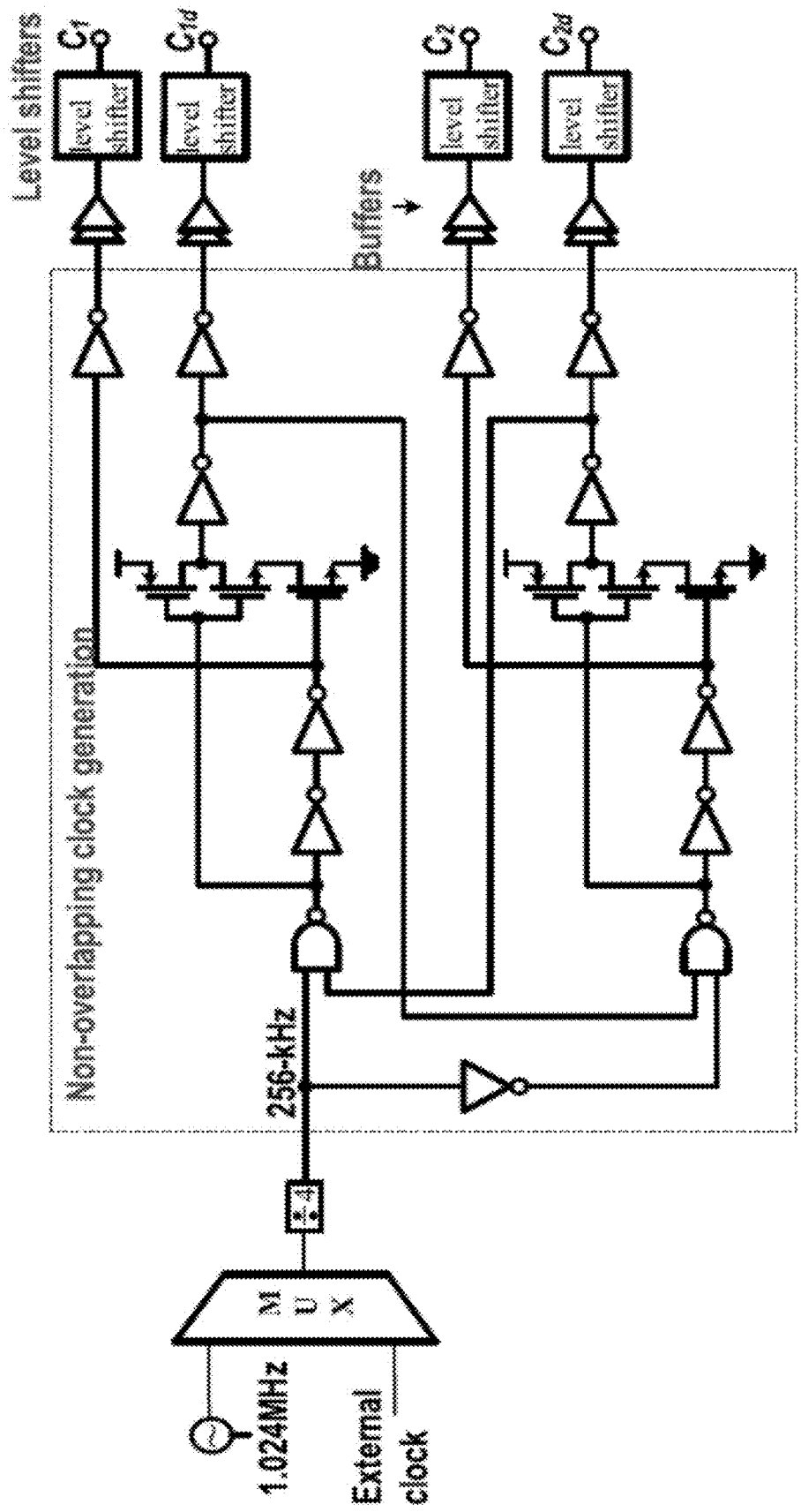

FIGS. 9A and 9B show diagrams depicting clock generation circuits including a 1.024-MHz ring oscillator and an 8-bit counter used to generate a 1-kHz signal from the sampling clock $C_1$ (FIG. 9A) and a non-overlapping clock generator followed by clock boosting (FIG. 9B). The circuit diagram illustrates both the reference clock generation using a ring oscillator, and the method all other necessary internal clocks for ΔΣM, Sinc² filter, etc., are provided. The modulator $V_{RP}/V_{RN}$ is near-$V_{DD}$ and ground, respectively, implemented by using an ultra-low voltage biasing circuitry operating in a subthreshold regime.

Example Transmitter (TX) Architecture

In the example architecture, output bits from ΔΣ M are passed through a sinc² decimation filter, and stored in a FIFO until the TX is activated. In various embodiments, the wireless biosensor in accordance with the disclosed technology employs a power oscillator-based transmitter. Power oscillator-based transmitters can be used in low-power wireless sensing systems due to their low complexity and low leakage power, which is particularly important for applications where the TX has a short active time and a low average data rate.

However, when the supply voltage continues going down, design challenges appear due to reduced switch ON conductance and reduced transistor transconductance, $g_m$. At a 0.6 V supply, for example, binary-weighted cross-coupled pairs are used instead of tail current sources to maximize $V_{GS}$ and $g_m$ of the cross-coupled input devices. When the supply voltage goes down further and below threshold voltage, for example, both $g_m$ and ON conductance become very small, and thus, extremely large devices are required to satisfy the start-up condition, which increases parasitic capacitance and thereby reduces the effective possible size of the radiating/resonant inductive antenna. At even 0.4 V, for example, the gates of the cross-coupled input pair, $M_{1,2}$ (FIG. 10A) are not sufficiently driven. Boosting the gate voltage can reduce the switch ON resistance and loss, but the low $g_m$ issue is still not resolved.

Alternatively, utilizing dc-dc converter to boost the power oscillator's $V_{DD}$ can improve $V_{GS}$ and $g_m$ of $M_{1,2}$, but the large ON current during the TX active state requires large power inductors and capacitors, which may not be suitable. In some example embodiments, a direct-RF power oscillator TX with a clamped body bias booster circuit is used to increase $g_m$ at 0.3-0.4 V, which, for example, can improve $g_m$ of cross-coupled pair by 29.6% and reduces the start-up time by 48%.

Example Ultra-Low Voltage Transmitter Circuit Design

In some embodiments, the TX is designed as a single-stage direct-RF OOK-modulated power oscillator (RFPO) that provides inherent impedance matching with a 1-cm 920 MHz on-board loop antenna.

Figure 10A:
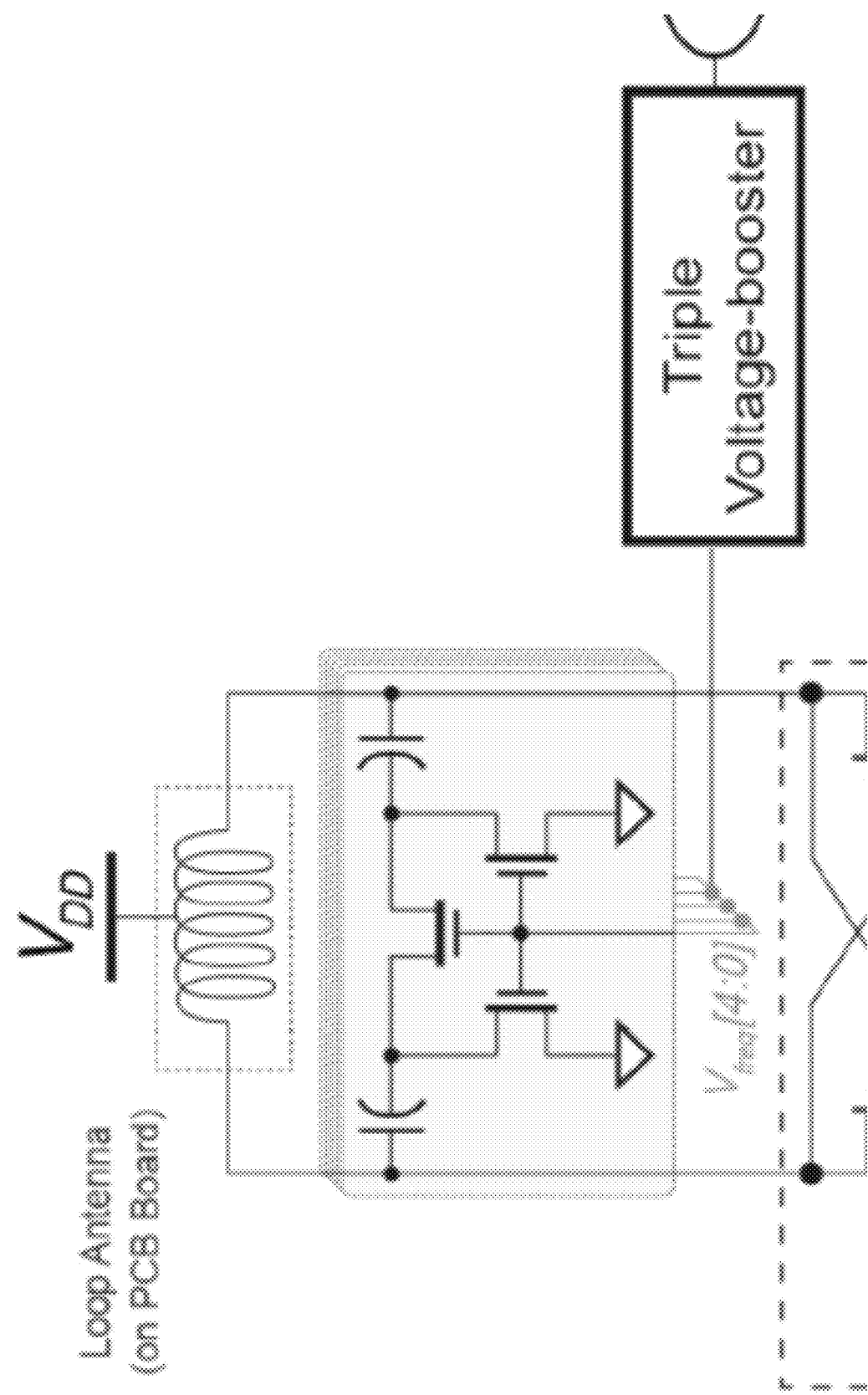
FIG. 10A shows a circuit architecture of an example embodiment of an ultra-low-voltage transmitter (TX), which includes a power oscillator, a clamped body bias voltage booster, and a 3× voltage booster.
Figure 10B:
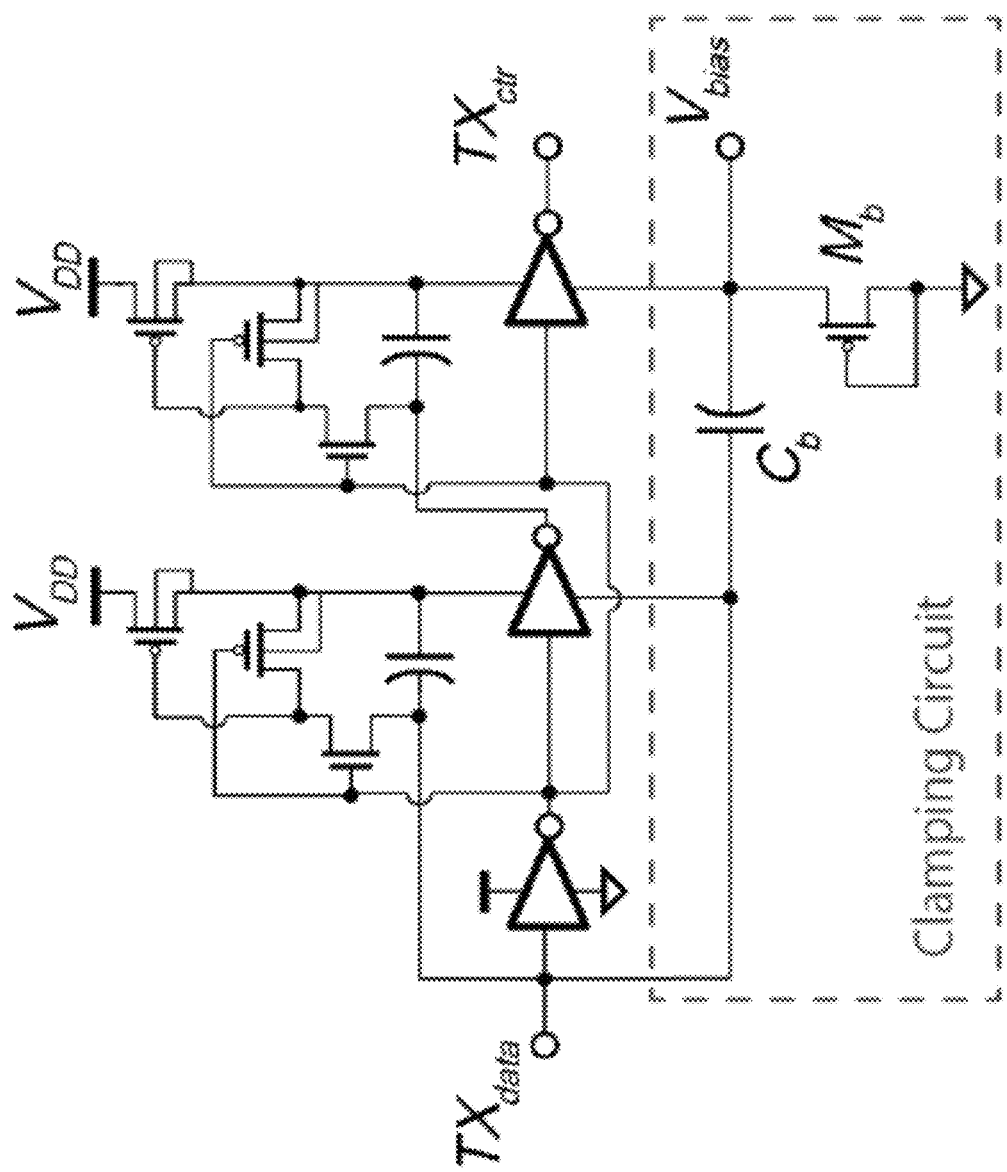
FIG. 10B shows a diagram of an example embodiment of the clamped body bias voltage booster shown in FIG. 10A.

FIG. 10A shows a circuit architecture of an example embodiment of an ultra-low-voltage transmitter (TX), which includes a power oscillator, a clamped body bias voltage booster, and a 3× voltage booster. FIG. 10B shows a diagram of an example embodiment of the clamped body bias voltage booster shown in FIG. 10A.

Prior to data transfer to the TX, the 5-bit capacitor array is activated by a 3× voltage booster in order to minimize the switch ON resistance and loss. The value of the capacitor connected to the LC tank is set by the 5-bit control code $CTR_f[4:0]$. When $TX_{data}$ goes high, $TX_{ctr}$ is boosted via a 3× clock boosting circuit to drive $M_0$ into triode mode, decreasing the ON resistance of $M_0$ by 94%. This helps increase the headroom and overdrive of $M_{1,2}$.

Figure 11:
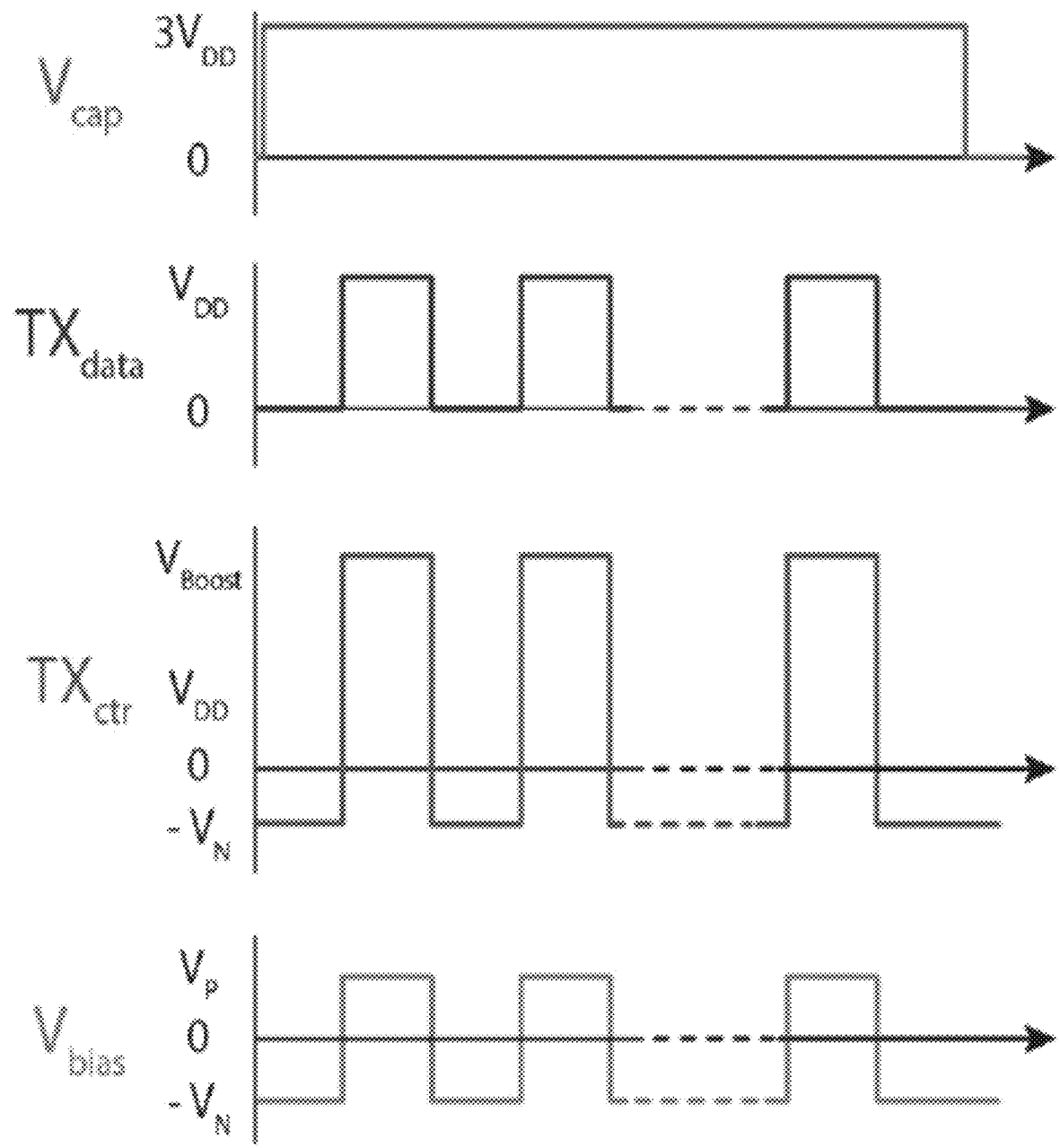
FIG. 11 shows a diagram depicting example waveforms of key signals in the transmitter shown in FIG. 10A.

FIG. 11 shows a diagram depicting example waveforms of key signals in the transmitter shown in FIG. 10A. To further increase $g_m$ of the input pair, a clamped clock boosting circuit FIG. 10B is used to set the body bias voltage, $V_{bias}$, to a positive potential, as illustrated in FIG. 11. Capacitor $C_b$ and diode-connected transistor, $M_b$, form a high-pass filter. When $TX_{data}$="1" $V_{bias}$ is near threshold voltage of clamping transistor $M_b$ due to the high resistance of $M_b$ in cutoff region, therefore increasing $g_m$ of $M_{1,2}$ by 29.6% and decreasing the start-up time by 48%.

Leakage currents can cause a slow voltage droop, which potentially affects the performance. But, the voltage droop speed is only 2 mV/Ωs ($C_b$=460 fF), according to simulation result, which makes the effect negligible as the TX data rate is >1 Mb/s. The extra gate driving strength of $M_{1,2}$ also minimizes the device size and parasitic capacitance by 75.5% iso-current, enabling a 0.7 mm larger antenna diameter while maintaining resonance at 920 MHz. At the falling edge of $TX_{data}$, $V_{bias}$ is set to a negative value about $V_{th}$-$V_{DD}$, which drives $M_0$ into super-cutoff region, and thus, helps reduce the off-leakage by 92%. Deep N-well transistors are used for $M_1$ and $M_2$ so that the body voltage can be adjusted without affecting other parts of the circuits. Given the rapid start-up time, the TX is deeply duty-cycled and activated once every 14.3 ms. When $TX_{data}$ is "0" $TX_{ctr}$ is set to "0", which turns $M_0$ OFF and thus, the TX is disabled and placed in a low-leakage state.

Example Biofuel Cell Design Architecture

Figures 12A, 12B:
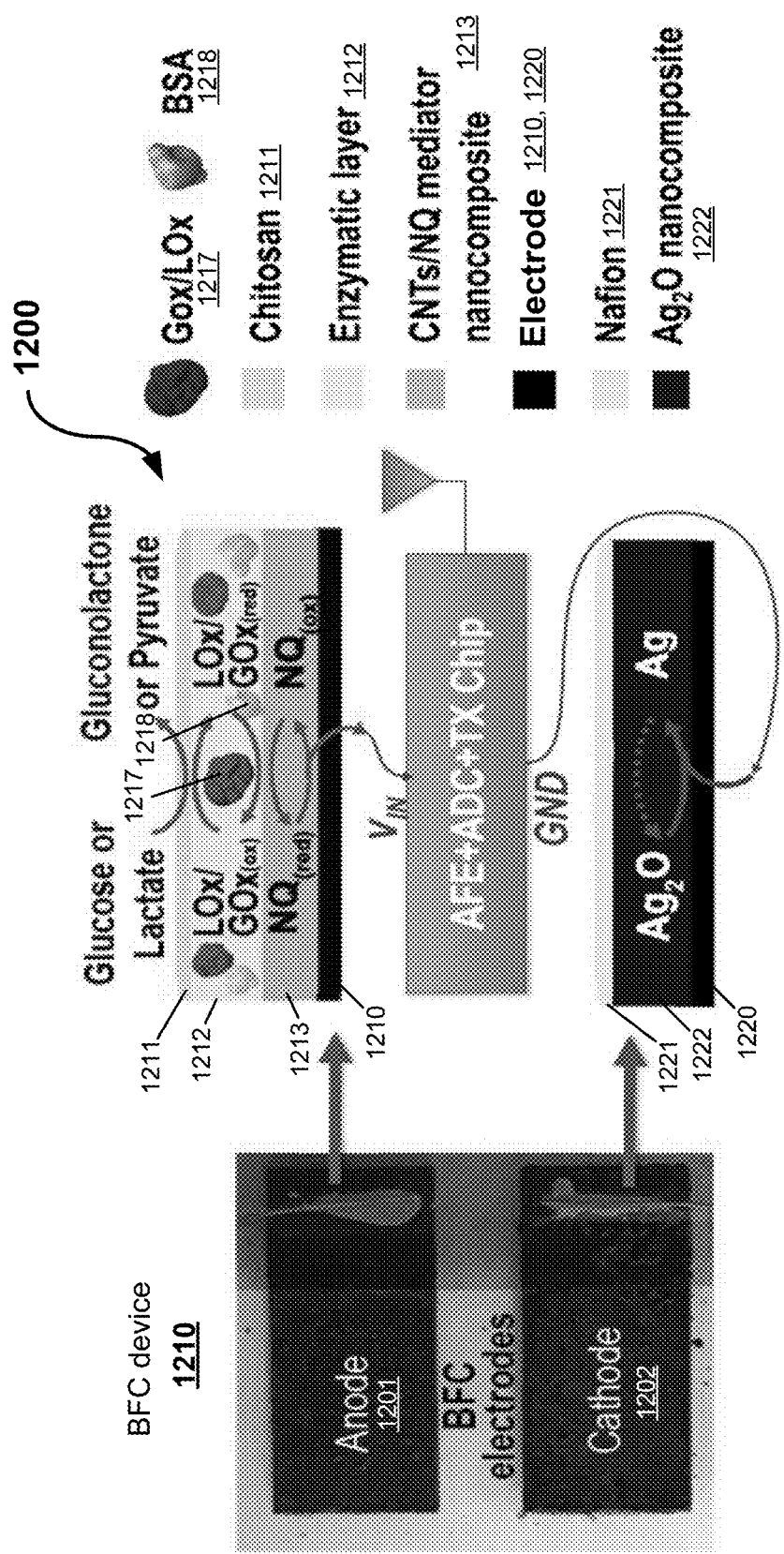
FIGS. 12A and 12B show diagrams of an example implementation of the example BFC-powered wireless glucose/lactate biosensor system in accordance with the present technology, including representative process pathways in the example BFC-powered biosensor system.

FIGS. 12A and 12B show diagrams of an example implementation of the example BFC-powered wireless glucose/lactate biosensor system 1200 in accordance with the present technology, including representative process pathways in the example BFC-powered biosensor system. An example biofuel cell device 1210 shown in FIG. 12A includes an anode contingent 1201 (also referred to as a BFC anode or bioanode) and a cathode contingent 1202 (also referred to as a BFC cathode or cathode). In this example, the bioanode 1201 is configured as an oxidase enzyme-based electrode, in which the bioanode 1201 includes an electrically-conducting electrode 1210 modified with a nanocomposite 1213 (e.g., carbon nanotubes with 1,4-naphthoquinone (NQ) mediator nanocomposite), an enzymatic layer 1212 (e.g., LOx or GOx 1217 and bovine serum albumin (BSA) 1218), and a chitosan layer 1211. The cathode is configured as an $Ag_2O$-based nanocomposite electrode, in which the cathode 1202 includes an electrically-conducting electrode 1220 modified with a $Ag_2O$ nanocomposite layer 1222 and a Nafion layer 1221. For example, the bioanode configuration is designed to facilitate a metabolite oxidation reaction (e.g., glucose or lactate oxidation), induced by the biocatalytic activity of oxidase enzymes (e.g., glucose oxidase (GOx) or lactate oxidase (LOx), respectively). In some example implementations of the BFC device 1210, the bioanode can be immobilized with an enzyme (e.g., GOx and/or LOx) and 1,4-naphthoquinone (NQ) as an electrochemical redox mediator.

When adding glucose or lactate, these metabolite fuels are oxidized, hence releasing electrons which are subsequently transferred to the anode. The small organic electron transfer NQ mediator can shuttle electrons between the enzyme active site and the electrode surface, enabling improved output power. Note that, inherently, oxidase-type enzymes (e.g., GOx and LOx) are renewable with the presence of $O_2$. Without refueling the enzyme, the active site of enzyme (e.g., Flavin groups, or FAD and $FADH_2$) can be recycled as the following reactions:

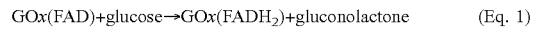

$$GOx(FAD)+glucose \rightarrow GOx(FADH_2)+gluconolactone \quad (Eq. 1)$$

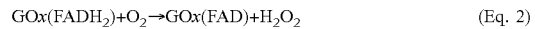

$$GOx(FADH_2)+O_2 \rightarrow GOx(FAD)+H_2O_2 \quad (Eq. 2)$$

where $FADH_2$ and FAD are Flavin adenine dinucleotide redox cofactor. With oxygen, $FADH_2$ (hydroquinone form) can release two electrons and two protons to recycle back to become the active FAD.

On the cathode side, for example, the $Ag_2O$ (e.g., existing in the nanocomposite) receives scavenged electrons.

Notably, both oxidase enzymes (GOx and LOx) naturally enable high selectivity, which can eliminate the need for a membrane to separate the reaction compartments.

Example Biofuel Cell Fabrication Methods

In some embodiments, a BFC device can be fabricated using the following techniques and materials, such as the example BFC device 1210 shown in FIGS. 12A and 12B. For example, BFC anodes can be fabricated by using a carboxylated carbon nanotube (CNT)-based mediator nanocomposite onto a current collector layer of a carbon-coated Cu sheet. The mediator nanocomposite includes a mixture of CNTs and NQ with the chitosan as a binder. For example, it is noted that the Cu sheet and CNTs can be employed to offer low BFC self-resistance. The anode functionalization can then be followed by an enzymatic layer, e.g., including LOx or GOx and bovine serum albumin (BSA). Glutaraldehyde solution can be used to cross-link amines in enzyme components. The bioanode immobilization was entrapped with the biocompatible chitosan layer.

The BFC cathode can include a carboxylated-CNT/$Ag_2O$ nanocomposite with Nafion as a binder. The $Ag_2O$ nanocomposite can be coated on a current collector of a carbon-coated Cu sheet cathode. Nafion can be laminated on the cathode.

In example implementations of the BFC device, BFCs were tested with glucose and lactate concentration in the 5-to-15 and 2.5-to-15 mM ranges, respectively, which is representative of the ranges present in various bodily fluids.

Example Results

This section discusses the example measurement results of the sampling ΔΣM, the wireless TX, and the in vitro glucose/lactate testing results for the example self-powered wireless biosensing chip implemented in a 65-nm LP CMOS technology.

Figure 13:
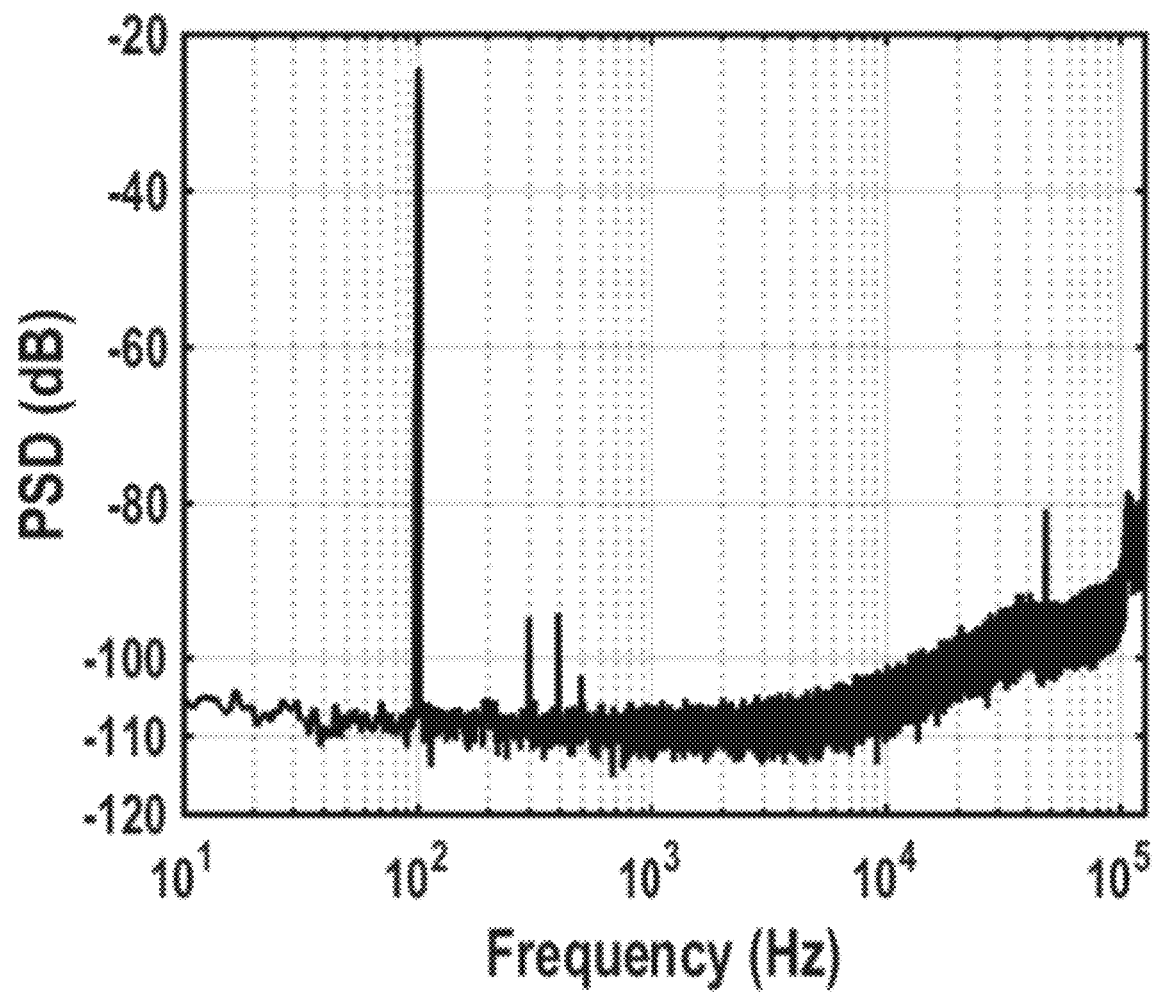
FIG. 13 shows a data plot depicting measured ΔΣM power spectral density (PSD) versus normalized frequency for a 100 Hz sinusoidal input with 250 $mV_{p\text{-}p}$ at $V_{DD}=0.3V$.

FIG. 13 shows a data plot depicting measured ΔΣ M power spectral density (PSD) versus normalized frequency for a 100 Hz sinusoidal input with 250 $mV_{p-p}$ at $V_{DD}$=0.3V.

Figure 14:
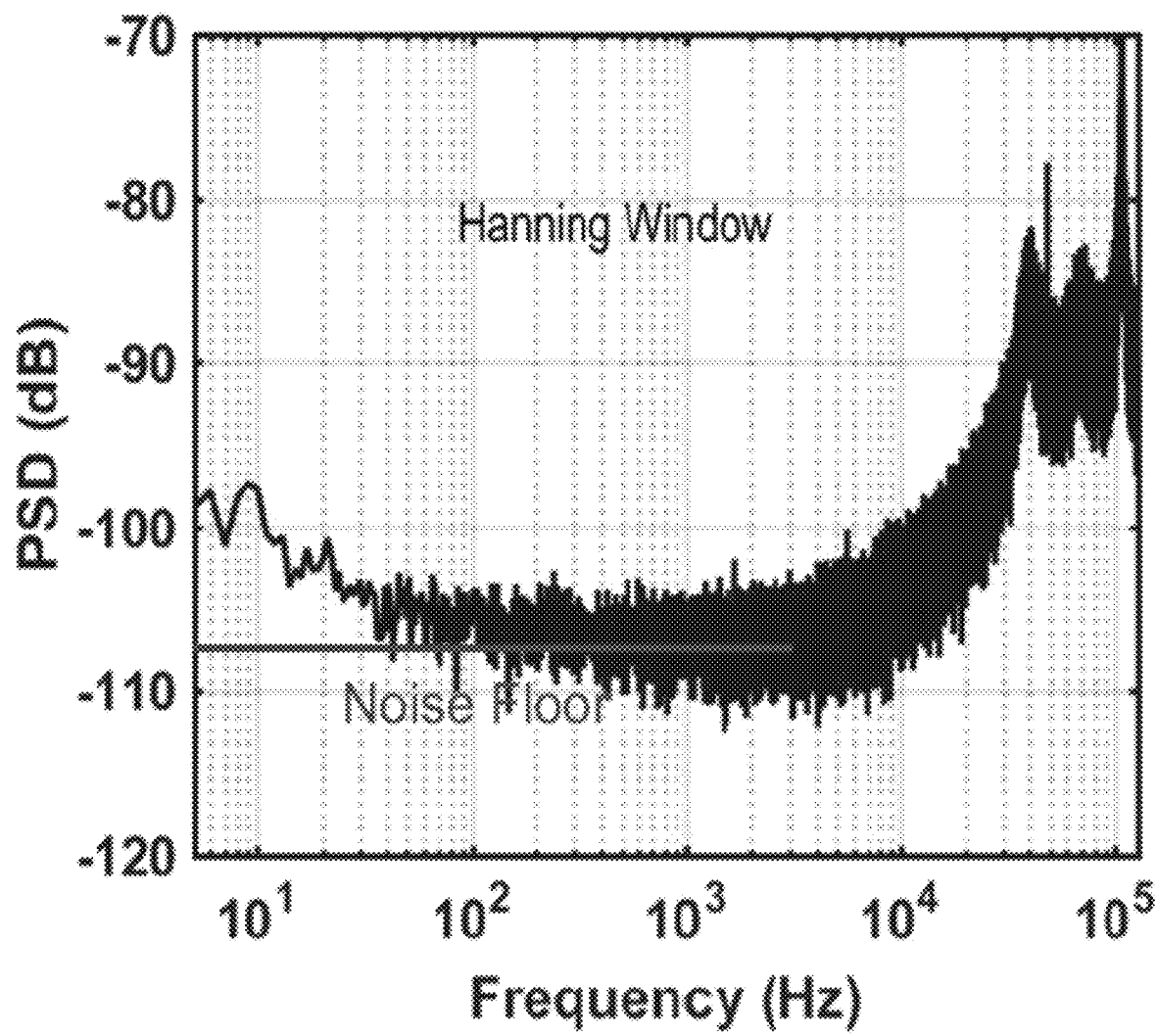
FIG. 14 shows a data plot depicting measured ΔΣM PSD versus normalized frequency with shorted inputs.

FIG. 14 shows a data plot depicting measured ΔΣ M PSD versus normalized frequency with shorted inputs.

The output spectrum of the ΔΣM, sampled at a 256 kHz clock frequency during active mode, is shown in FIG. 13, indicating 64 dB SNR, 60 dB SNDR, and 65 dB dynamic range (DR), respectively, for a 3 kHz signal bandwidth. The ADC including digital decimation filter consumes 180 nW power at 0.3 V. The zero input SNDR measurement in FIG. 14 shows that no tones are present in the signal band.

Figure 15:
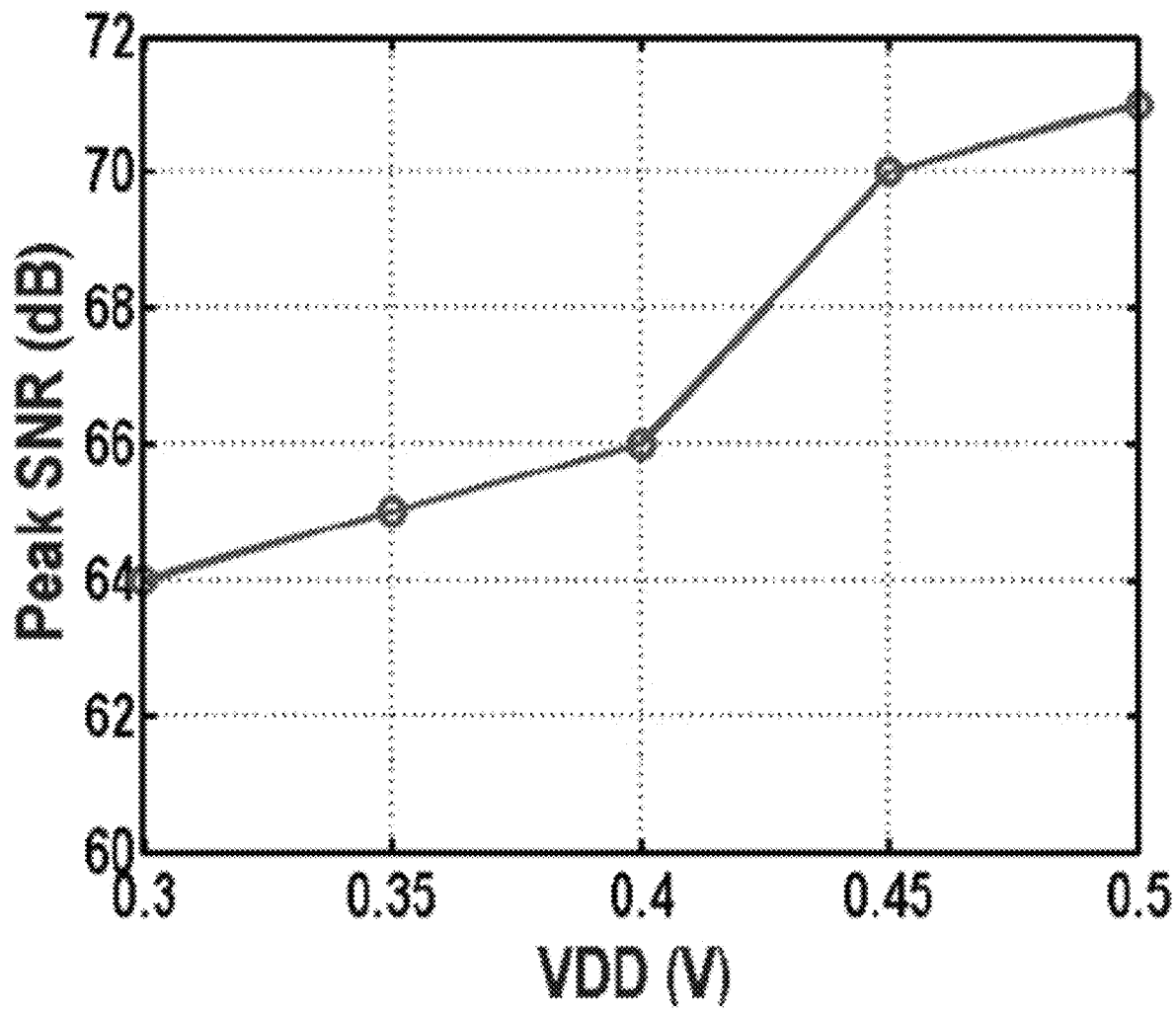
FIG. 15 shows a data plot depicting signal-to-noise ratio versus power supply.

FIG. 15 shows a data plot depicting signal-to-noise ratio versus power supply. The data plot shows the modulator peak SNR across $V_{DD}$, demonstrating robustness to supply voltage variation, while achieving up to 71 dB SNR and 65.5 dB SNDR at 0.5 V.

Figure 16:
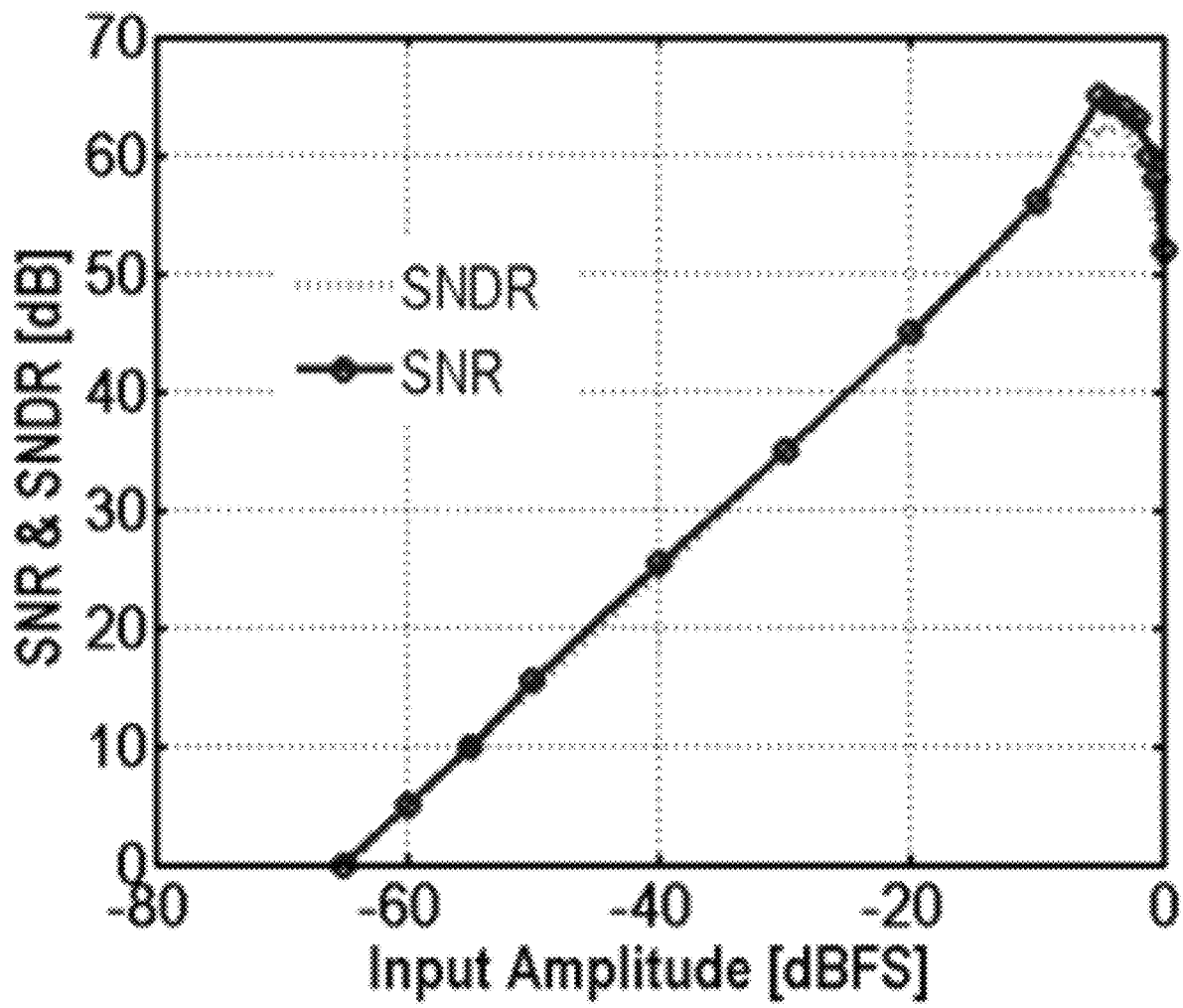
FIG. 16 shows a data plot depicting signal-to-noise ratio (SNR) and signal-to-noise distortion ratio (SNDR) versus normalized input amplitude for a 100-Hz sinusoidal input.

FIG. 16 shows a data plot depicting signal-to-noise ratio (SNR) and signal-to-noise distortion ratio (SNDR) versus normalized input amplitude for a 100-Hz sinusoidal input. The measured SNR and SNDR curves are shown in FIG. 16, with input amplitude normalized by the reference voltage. The estimated DR is 65 dB from a 300-mV supply voltage.

A 10-bit ADC is designed for possible operation of ΔΣ ADC at lower supply voltages as SNR degrades significantly at 0.23-0.25 V. Also, 10-bit ADC enables possible extension of the application to a wider DR for sensing metabolite concentrations much smaller than 2 mM.

Implemented fully differentially in a 30 μm×650 μm of core area, the example ΔΣ ADC achieves a figure-of-merit (FoM) of 37 fJ/conv.-step at 0.3 V. For example, the obtained FoM is 8× better than a previous 2nd-order passive modulator operating at a 0.7-V supply and 12.9× better than a near-threshold-voltage inverter-based modulator operating at 300 mV. During inactive mode, the ADC consumes only 2 nW.

Figure 17A:
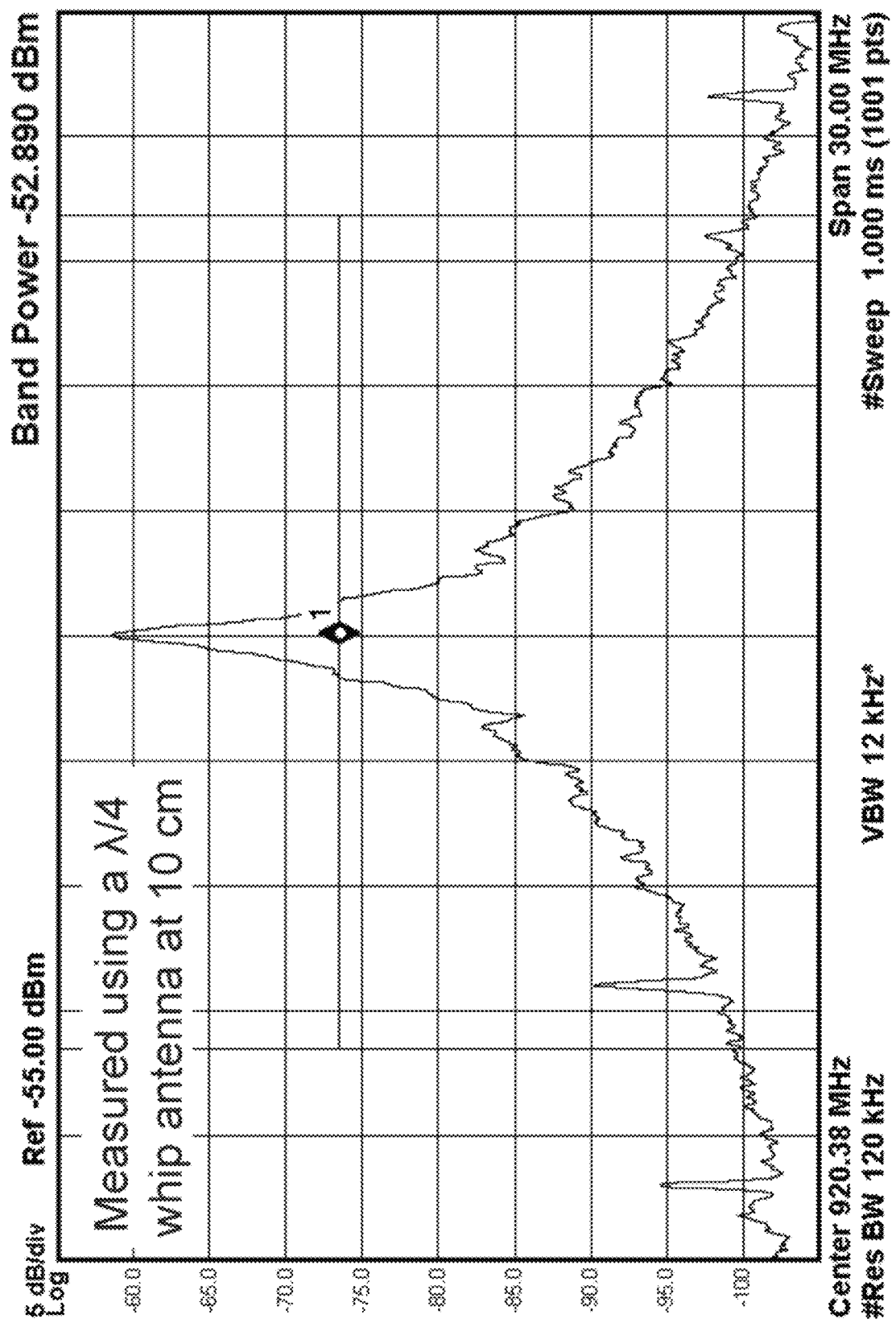
FIGS. 17A and 17B show data plots depicting measured transmitter power spectrum (FIG. 17A) and transmitter start-up time (FIG. 17B).
Figure 17B:
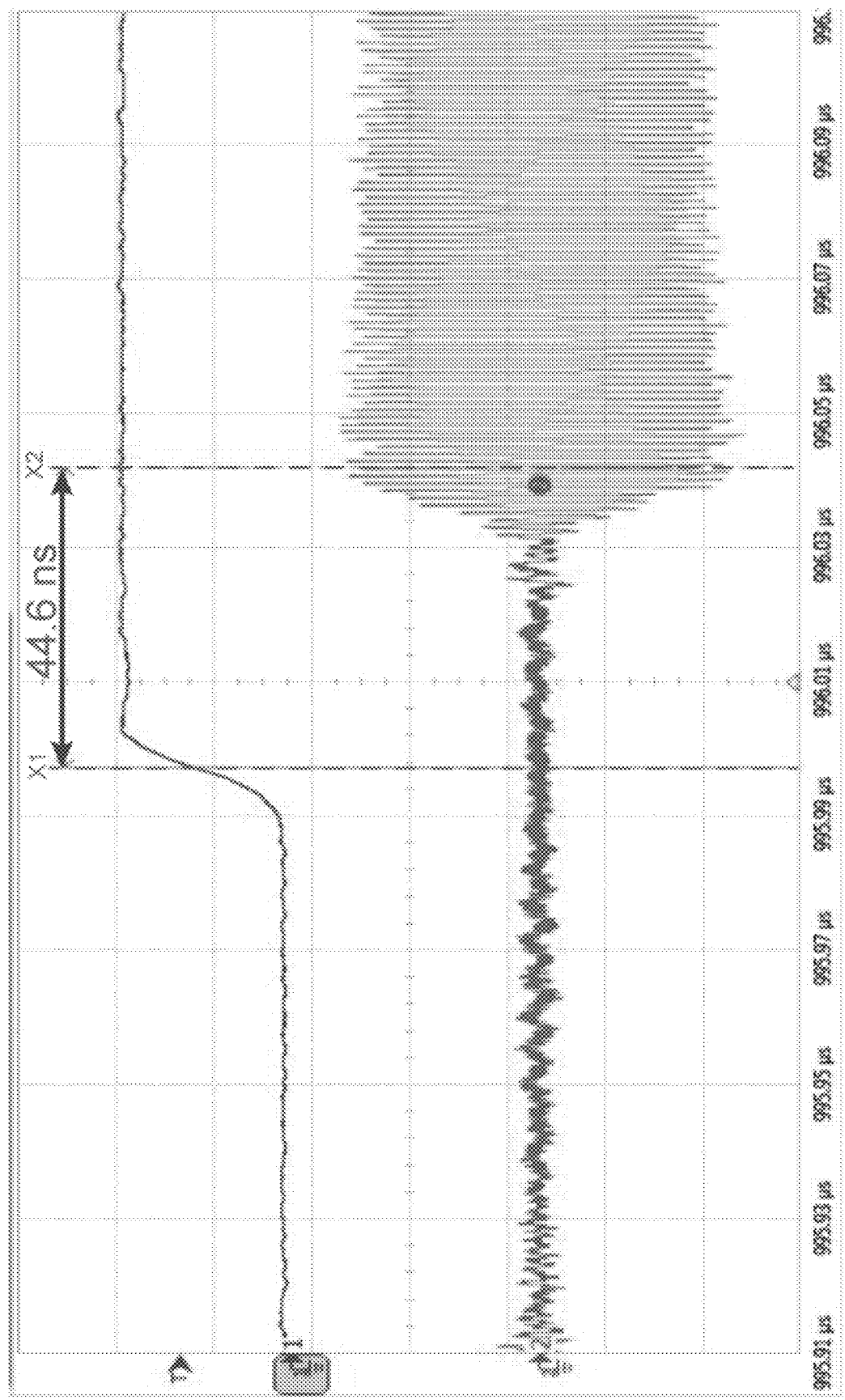

FIGS. 17A and 17B show data plots depicting measured transmitter power spectrum (FIG. 17A) and transmitter start-up time (FIG. 17B).

In particular, the plot of FIG. 17A shows the TX power spectrum measured by placing a λ/4 whip antenna 10 cm away from the TX. With a center frequency of 920 MHz, the wirelessly received power is >−53 dBm (>−50 dBm) when the TX operates at 1 Mb/s (4 Mb/s), which consumes 30 pJ/bit (14.4 pJ/bit) at 0.3 V (0.35 V). The RFPO consumes 30.1 μW active power at 0.3 V, and 100 pW during the sleep mode. Its digital controller consumes 5 nW.

The time-domain waveforms of the transmitter are shown in the plot of FIG. 17B. Thanks to the clamped body bias voltage booster, the TX achieves less than 44.6-ns start-up time with a 0.3 V supply, improved by 14.2% compared to a former low-power low-supply counterpart which works at 0.6 V. Supply voltage variation may cause frequency deviation due to the changing parasitic capacitance.

When supply voltage changes from 0.3 to 0.5 V, the resonant frequency of the power oscillator deviates by 11 MHz according to the measurement results. For example, this may be mainly due to the pad electro static discharge (ESD) and transistors parasitic capacitance changing with supply voltage. However, with a given BFC, the open-circuit voltage of the BFC is relatively stable and will not have such a large variation, and the TX is essentially operating with a fixed supply voltage value. The activation of TX will cause a voltage drop but this effect can be attenuated by using a larger board decoupling capacitor.

To minimize the frequency deviation caused by open-circuit voltage variation among different BFCs and during long-term operation, pre-calibration and frequency compensation techniques are needed. Environmental changes, such as the presence of materials with conductivities or permittivities different than air, for example, the presence of the human body, can potentially also affect the resonant frequency of the TX. To test this, a human hand was waved over the antenna structure; at a distance of up to 5 mm away from the antenna, no appreciable changes to the resonant frequency were observed during measurements.

In vitro testing of the system was performed, where the glucose or lactate BFC was used as the sole source of power for the system.

Figure 18A:
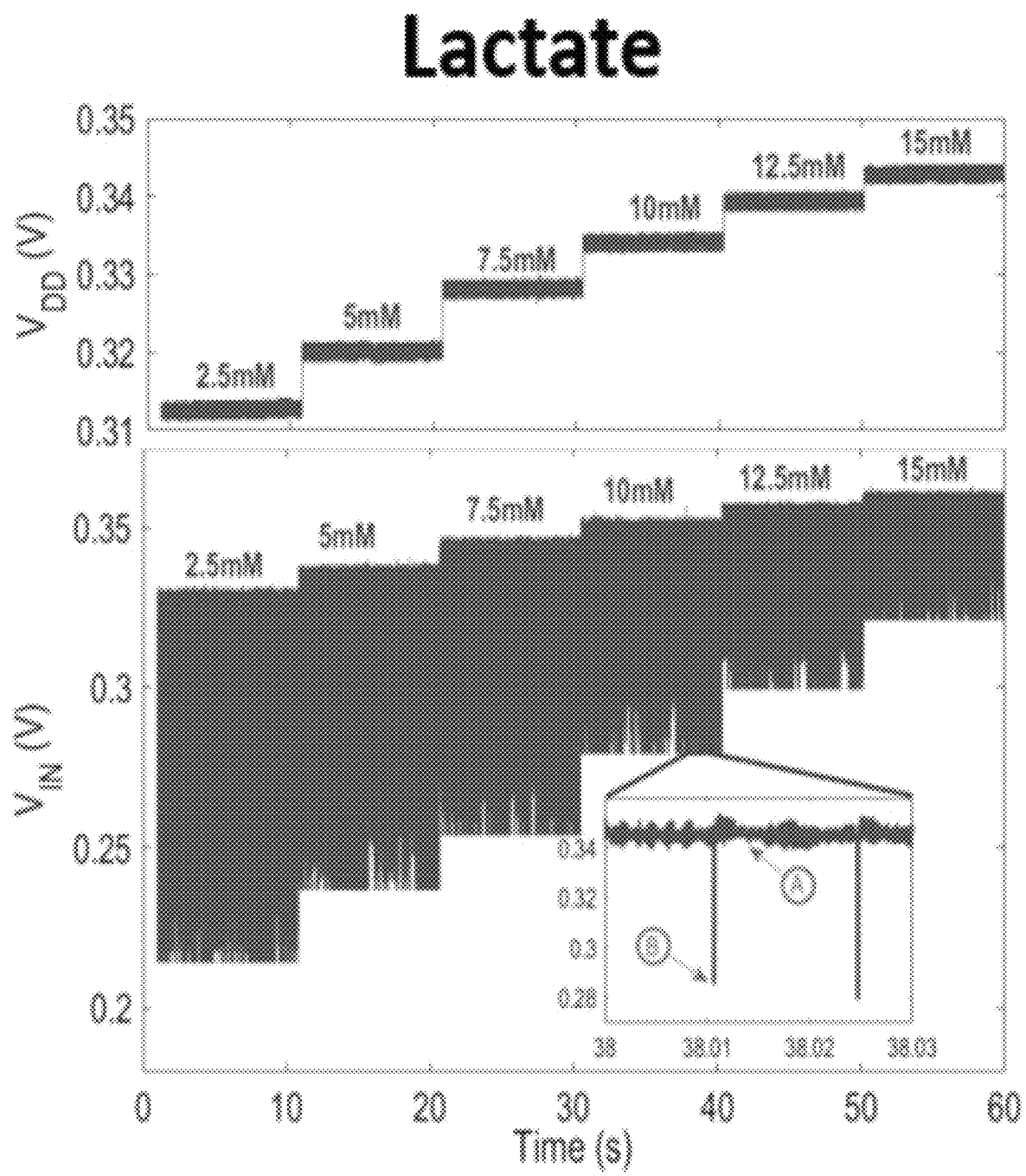
FIGS. 18A and 18B show data plots depicting measured dynamic $V_{DD}$ variation and $V_{IN}$ waveforms during in-vitro experiments for lactate (FIG. 18A) and glucose (FIG. 18B)
Figure 18B:
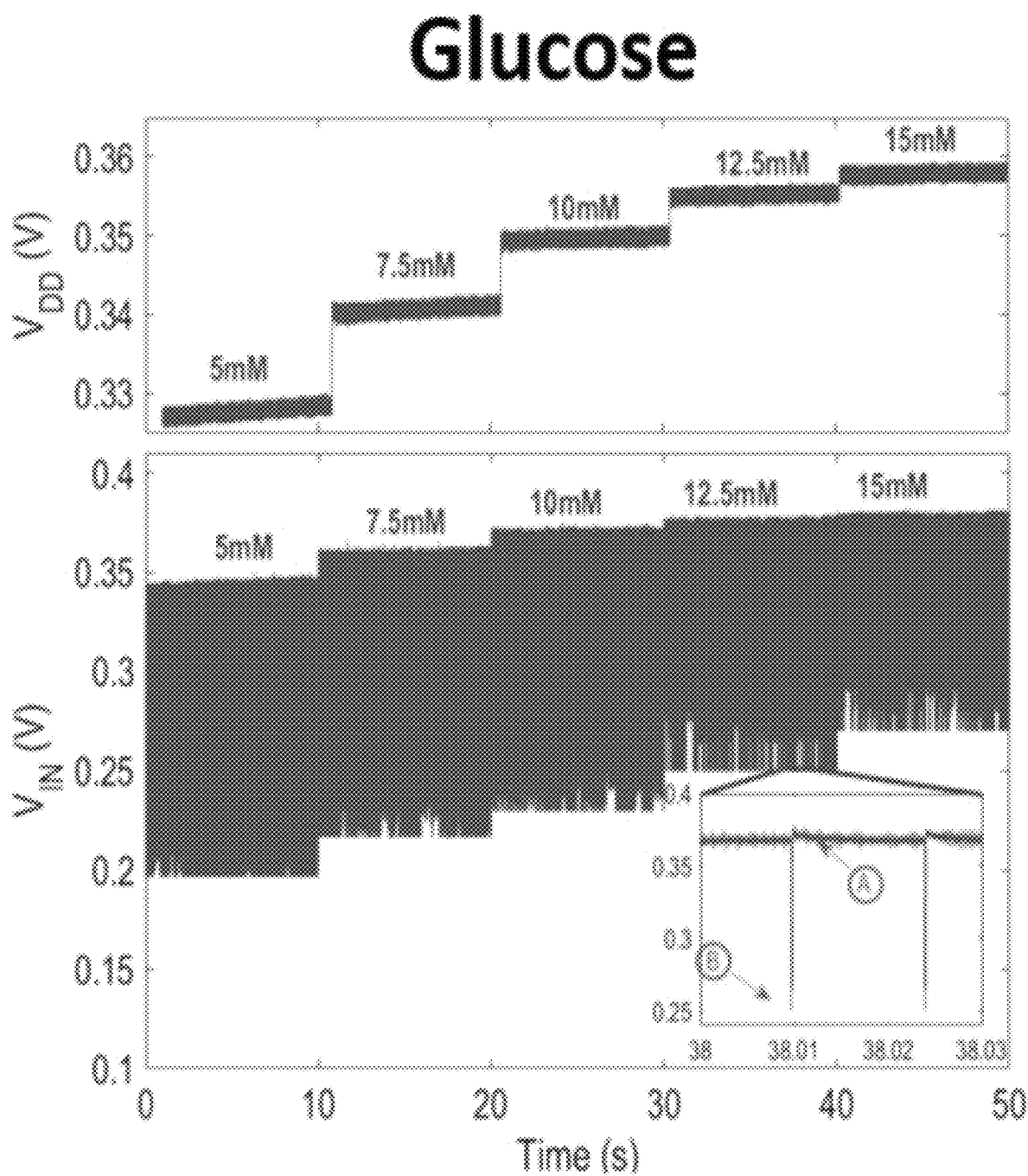

FIGS. 18A and 18B show data plots depicting measured dynamic $V_{DD}$ variation and $V_{IN}$ waveforms during in-vitro experiments for lactate (FIG. 18A) and glucose (FIG. 18B). As shown by these plots, the example system can operate from the BFC power source and can successfully detect changes in lactate or glucose concentration between, e.g., 2.5 and 15 mM for lactate or 5-15 mM for glucose.

Figure 18C:
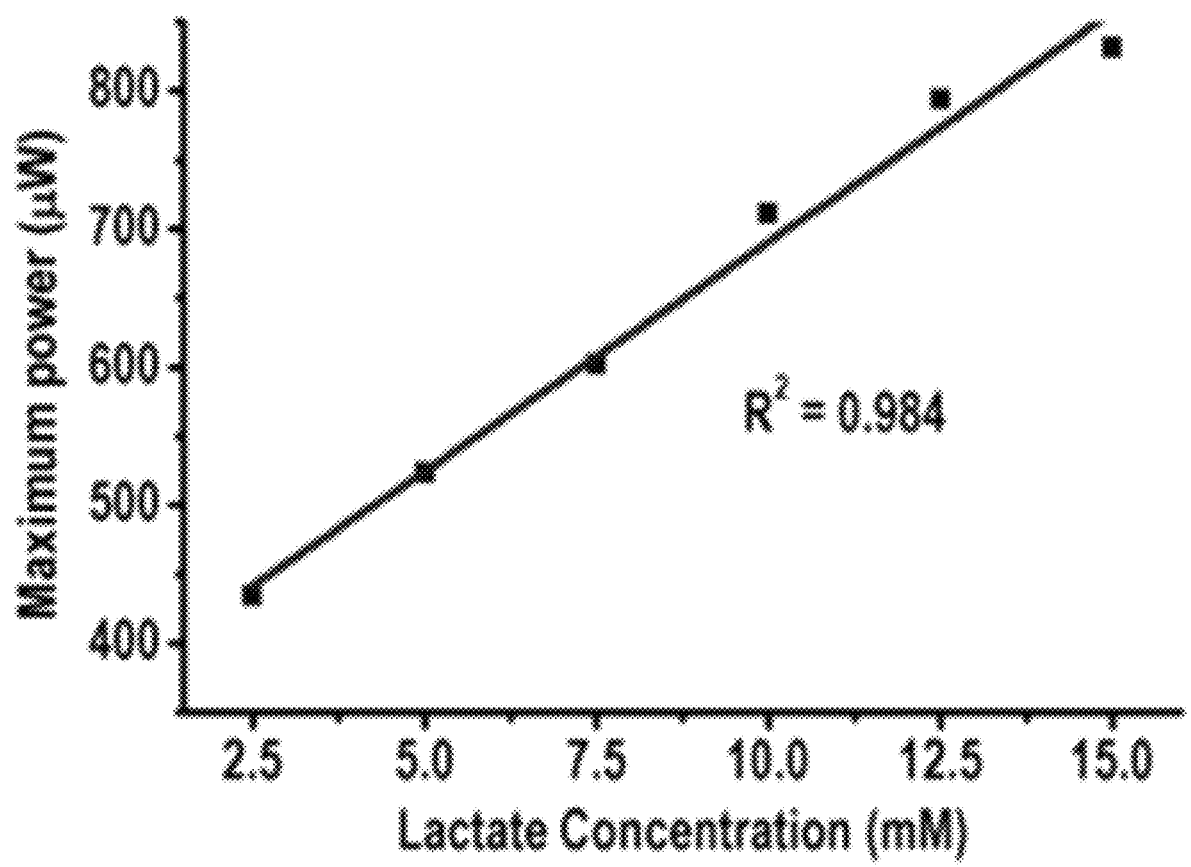
FIGS. 18C and 18D show data plots depicting calibration curves from the example measurements of FIGS. 18A and 18B, respectively.
Figure 18D:
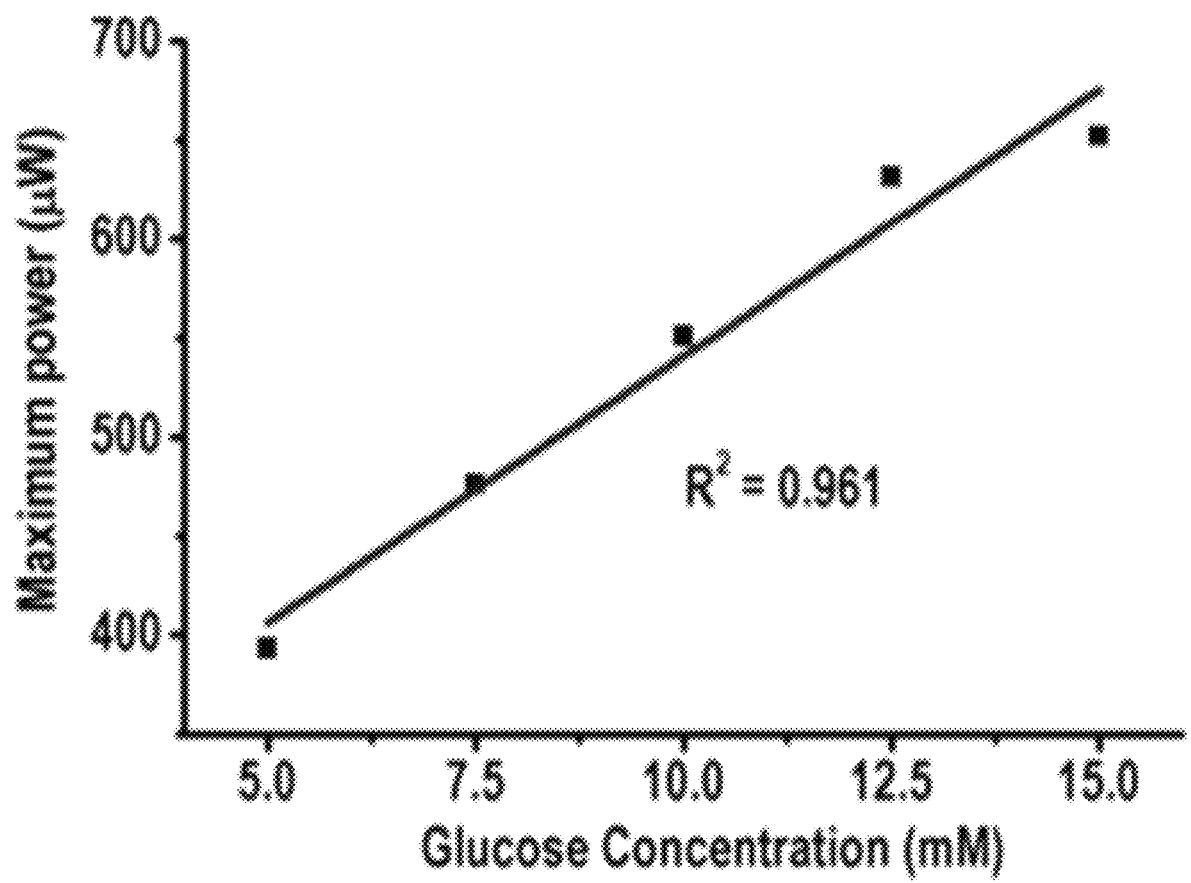

FIGS. 18C and 18D show data plots depicting calibration curves from the example measurements of FIGS. 18A and 18B, respectively. The correlation between analyte concentration and the MPP in both sets of experiments was high, e.g., R2=0.984 and 0.961 for lactate (FIG. 18C) and glucose (FIG. 18D), respectively. The power output begins to saturate at high-concentration levels due to increased enzymatic kinetics, which would require careful characterization and calibration in a clinical use.

Figure 19:
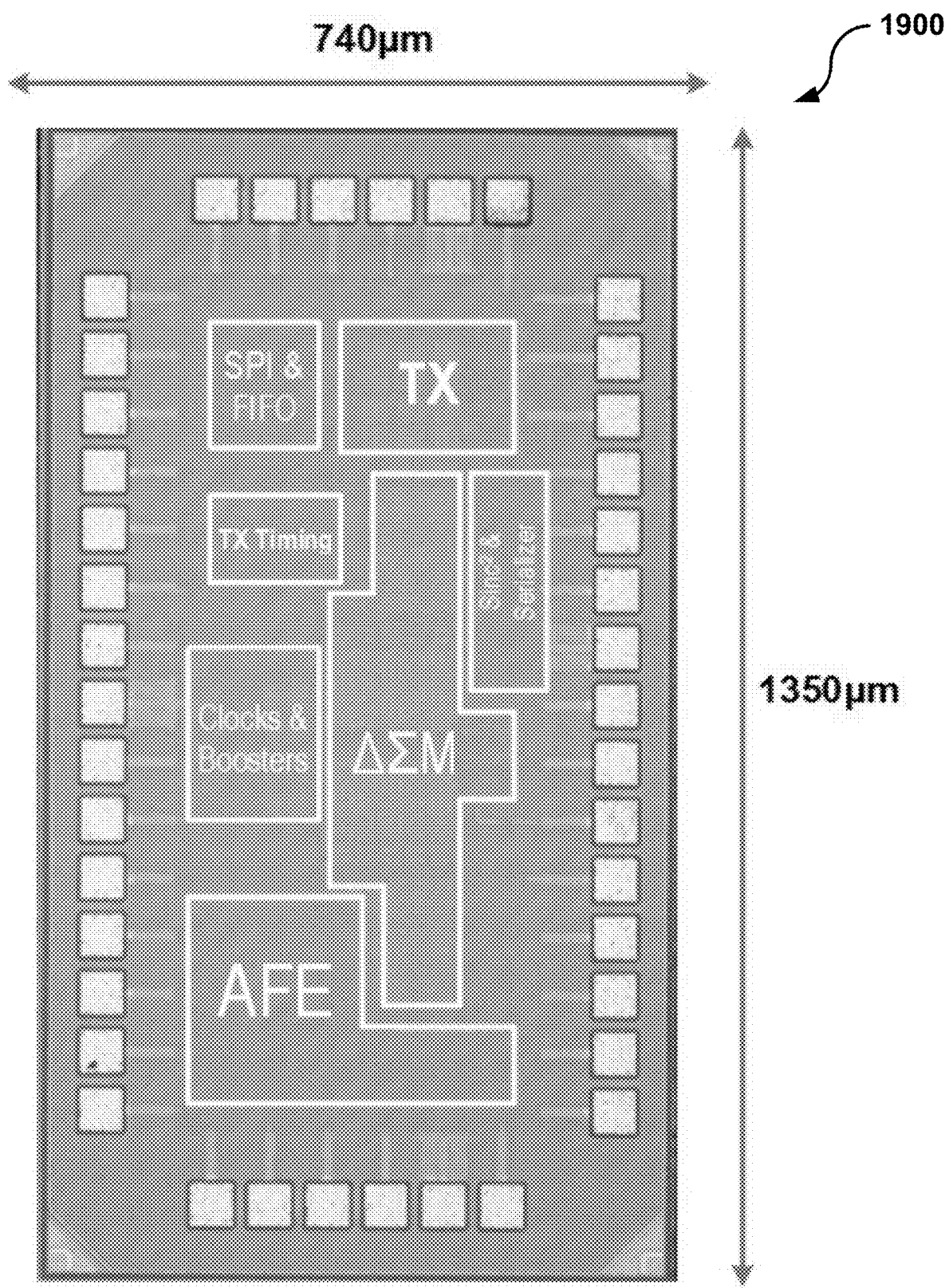
FIG. 19 shows a die micrograph of an example embodiment of a BFC-powered wireless biosensing system in accordance with the disclosed technology.

FIG. 19 shows a die microphotograph of the example BFC-powered wireless chip 1900 implemented based on an embodiment of the disclosed technology. The example BFC-powered wireless chip 1900 includes a serial peripheral interface (SPI), a first-in-first-out (FIFO) buffer, a transmitter (TX), ΔΣ modulator (ΔΣM), a TX timing circuit, clock generators and boosters, and an analog front-end (AFE). In some embodiments, a circuit design of the BFC-powered wireless chip 1900 includes the circuit shown in FIG. 1A.

As discussed above, the disclosed devices, systems and methods are able to sense metabolites (e.g., glucose, lactate) without requiring any external power source. The power from the biofuel (the metabolite) is used to directly power an analog-to-digital converter and wireless transmitter. The circuits used for sensing are designed to operate directly at the BFC voltage (e.g., down to 0.25V), eliminating the need for a DC-DC converter, which saves implementation area (e.g., no inductor required). The sensor is duty-cycled such that the BFC only operates at the maximum-power point for a brief period of time, necessary to extract the biofuel concentration, before reverting to a low-power state. For example, this can improve the longevity of the sensor.

In an embodiment of the disclosed technology, a biosensing system having a biosensor for detecting analytes in glucose or lactate may include integrated circuits, an anode including a first nanocomposite, an enzymatic layer electrically coupled to a power supply voltage terminal of the integrated circuits and being configured to interact with the glucose or lactate, and a cathode including a second nanocomposite electrically coupled to a ground voltage terminal of the integrated circuits. Here, the integrated circuits use power generated while the glucose or lactate is being decomposed by the first nanocomposite of the anode.

Also disclosed are ingestible devices, systems and methods for sensing metabolites while using the power from a biofuel (e.g., the metabolite) to directly power an electric circuit, without requiring any external power source.

Electrochemical wearable devices are getting more attention thanks to the information they can provide to improve health and activity applications. Yet, power management of these biosensing systems has still been a challenging issue to address. Some low power design strategies have been introduced at the system-level and circuit-level to mitigate the power consumption challenge, yet these approaches may not be feasible to address power challenges as wearable devices become smaller and smaller.

As discussed above, a wireless physiochemical sensing system can monitor glucose or lactate when powered via an enzymatic biofuel cell (BFC) based on energy naturally present in the underlying analytes to be sensed have been presented.

In the following disclosure, example embodiments and implementations of an ingestible sensing capsule are described that enable self-powered sensing of analytes (e.g., glucose) in the body when swallowed.

Figure 20:
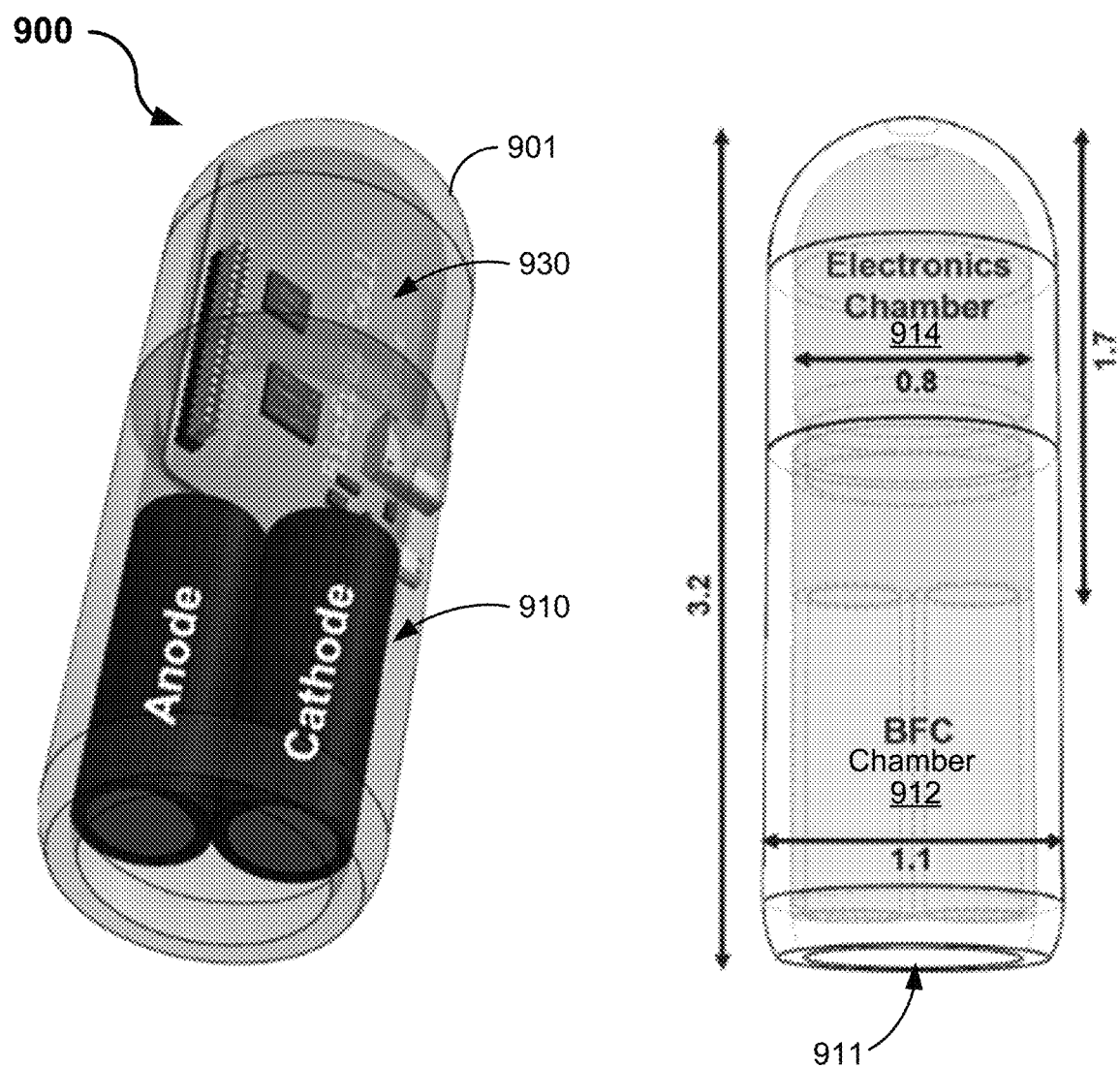
FIG. 20 shows a diagram of an example embodiment of an ingestible self-powered biosensing system configured in a capsule in accordance with the disclosed technology.

FIG. 20 shows a diagram of an example embodiment of an ingestible self-powered biosensing system 900 configured in a capsule in accordance with the present technology. The ingestible self-powered biosensing system 900 includes a capsule 901 that encapsulates a biofuel cell device 900 electrically coupled to an electronic circuit 930.

In some embodiments, the capsule 901 of the ingestible biofuel cell device 900 includes a curved cylindrical body encompassing a hollow interior and an opening 911 at one end of the capsule to the hollow interior. In such embodiments, the biofuel cell device 910 is contained in a first chamber within the hollow interior of the capsule 901 that is proximate the opening 911, such that the biofuel cell is operable to extract energy from a biofuel (e.g., metabolite) in a fluid, e.g., of a living organism that ingests the ingestible biofuel cell. In such embodiments, the electronic circuit 930 is contained in a second chamber within the hollow interior of the capsule 901 and coupled to the biofuel cell device 910. In some embodiments, the electronic circuit 930 includes an amplifier and a switch, where electrical energy (e.g., electrical current) from the extracted energy of the biofuel cell device 910 is supplied to an amplifier of the electronic circuit 930 to establish a supply voltage for the ingestible biofuel cell device 900.

In some embodiments, as shown on the right side of the diagram of FIG. 20, an example configuration of the capsule 901 shows size dimensions including a capsule length of 3.2 cm with a tapered diameter, where a diameter of the biofuel cell (BFC) chamber 912 is 1.1 cm and a diameter of the electronics chamber 914 is 0.8 cm. In such example embodiments, the electronic circuit 930 can be implemented in an area of less than 0.8 cm×1.7 cm, providing a small size regime with protective properties for various implementations of the ingestible self-powered biosensing system 900.

Figure 21:
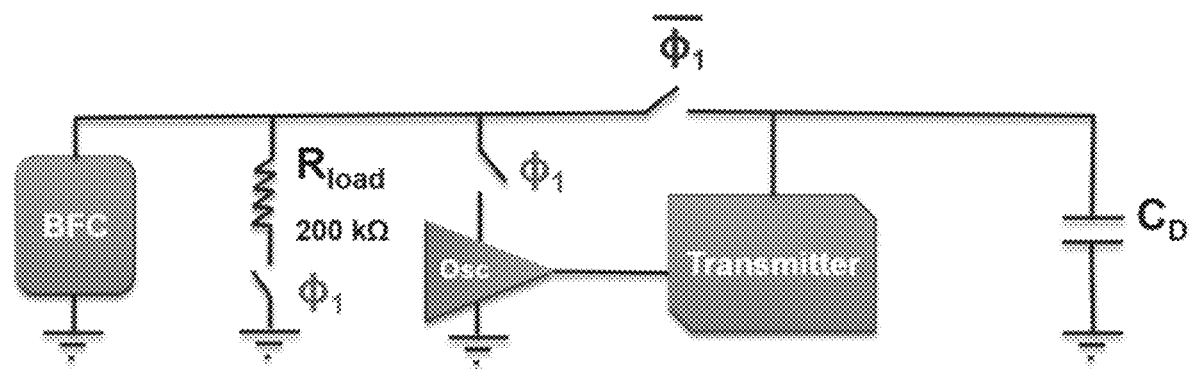
FIG. 21 shows a circuit block diagram of the example BFC circuit of the system shown in FIG. 20.

FIG. 21 shows a block diagram of an example embodiment of the ingestible self-powered biosensing system 900 shown in FIG. 20. This example configuration shows a behavioral description of the system during two phases of $\Phi_1$ and $\overline{\Phi}_1$. During phase $\Phi1$, a load resistance of the electronic circuit 930, e.g., of 200 kΩ, is connected to the terminal of the biofuel cell device 910 (e.g., "BFC" in the diagram). This load corresponds to an operating voltage, which its value depends on the concentration of the BFC fuel, e.g., glucose, lactate, or other metabolite. This voltage level gets converted to a frequency value by using a ring oscillator (shown as "Osc" in the diagram). The ring oscillator operates as a data converter that ultimately translates the concentration of glucose to a frequency level. In phase $\overline{\Phi}_1$, however, the matching load is not connected to the BFC, and the system can operate in a lower power mode. In some example implementations, the control voltage, e.g., for switching between these two phases, is internally generated by using some circuitries, such as the example described in FIG. 22.

Figure 22:
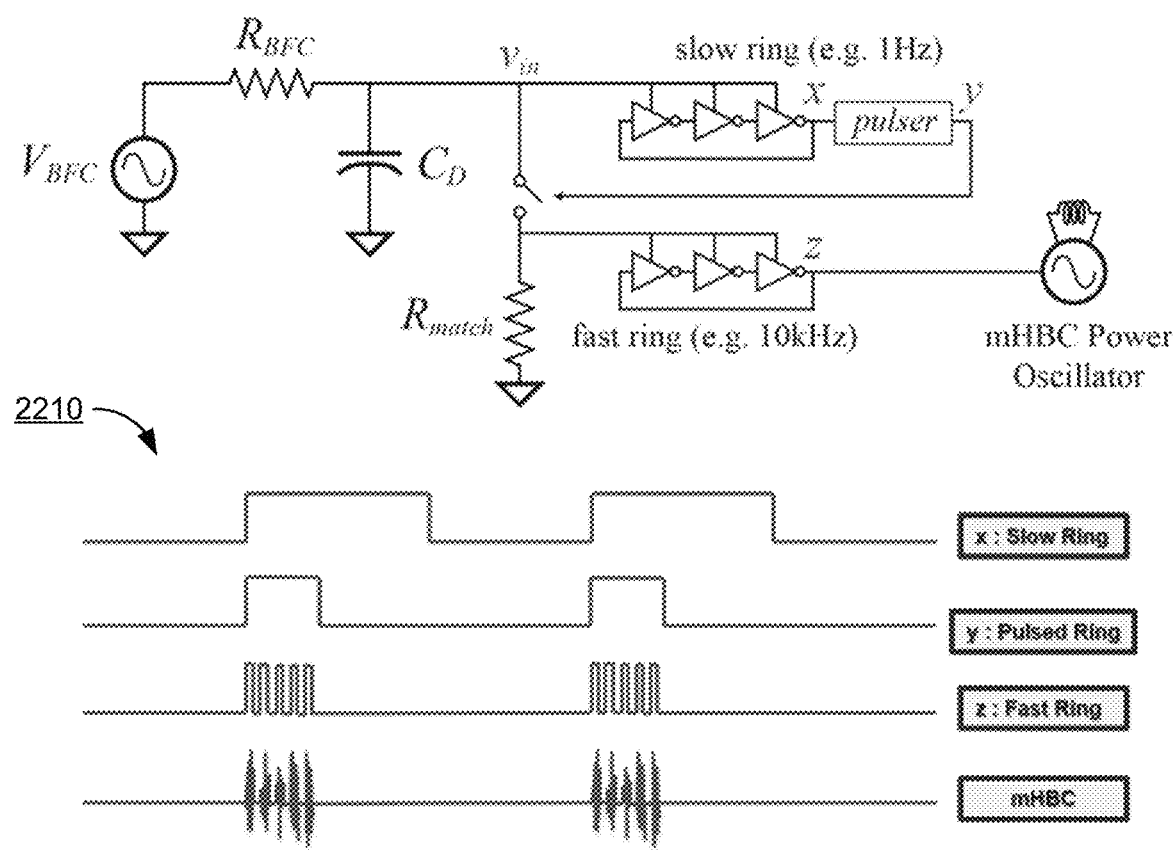
FIG. 22 shows a detailed circuit diagram of the example BFC circuit shown in FIG. 21.

FIG. 22 shows a detailed circuit diagram of the example BFC-interfaced circuit shown in FIG. 21. In some embodiments, for example, the circuit includes a slow ring oscillator, fast ring oscillator, pulser, an LC power oscillator, and off-chip PCB coil antenna. The slow ring oscillator, which sets frequency of data transmission, is duty cycled using the pulser to reduce the on-time of the circuit, thus reducing power consumption. The antenna doubles as the inductor for the power oscillator. Some additional circuit blocks are introduced to improve low voltage operation (e.g., 0.3V-0.6V).

The diagram of FIG. 22 represents an example embodiment of the ingestible self-powered biosensing system 900 using two ring oscillators (fast and slow ring oscillators), pulser, and an LC power oscillator using on-off keying modulation (OOK). The slower ring oscillator is configured to operate in a lower power mode at a potential near to the open circuit voltage of the BFC. This low frequency signal is duty cycled by a pulser to control the connection of $R_{match}$ to the BFC terminal. When the load is connected to the BFC, the faster ring oscillator kicks into the circuit. This oscillator operates at a higher power and lower voltage levels and generates higher frequency values. Particularly, the pulser duty cycles this mode to reduce the power consumption of the configuration. A timing diagram 2210 of the example circuitries are shown in the lower portion of FIG. 22.

As depicted in the timing diagram 2210, the fast ring signal has been duty cycled using the slower ring signal and the pulser. The output of the fast ring oscillator (e.g., the modulated carrier) is transmitted by using a mHBC power oscillator. Note that this modulated signal conveys information related to the approximate open circuit voltage as well as the voltage of BFC for the matching load (e.g., 200 kΩ). The frequency of envelope of the modulated carrier represents the approximate open circuit voltage, whereas the voltage of BFC for the matching load can be interpreted from the frequency of carrier. This data enables the receiver to back calculate the real-time concentration of glucose in the digestive system.

By choosing the optimal load line power point tracking resistor of the BFC, R_match, the voltage variation, proportional to glucose concentration, translates directly to frequency variation in a voltage-controlled oscillator (VCO). This frequency variation, e.g., data rate, modulates an LC power oscillator using on-off keying modulation (OOK). The output modulated signal from the LC power oscillator can be measured wirelessly and translated back to glucose concentration using fitted curves. In addition, for example, by using another VCO to generate the clock, the open-circuit voltage of the BFC can be determined by measuring the frequency of transmission.

Examples

In some embodiments in accordance with the present technology (example 1), a self-powered biosensing system for detecting an analyte includes an electronic circuit, including a signal converter and a switched or matched impedance load; an anode, including a first nanocomposite and an enzymatic layer, wherein the anode is electrically coupled to a power supply voltage terminal of the signal converter, when connected through the switched or matched impedance load of the electronic circuit, and is configured to interact with an analyte in a fluid, the analyte including glucose or lactate; and a cathode, including a second nanocomposite and electrically coupled to a ground voltage terminal of the electronic circuit, wherein electrical energy is generatable from transformation of the analyte to a derivative substance based on electrochemical reactions across the anode and cathode, wherein the electronic circuit is configured to control and utilize generated power from the electrochemical reactions across the anode and cathode to supply the generated power to components of the electronic circuit, and wherein the electronic circuit is operable to translate the electrical energy as transmittable digital data associated with a concentration of the analyte.

Example 2 includes the system of example 1, wherein the electronic circuit is able to operate directly from the generated power using a maximum power point across the anode and cathode to infer the concentration of the analyte in the fluid.

Example 3 includes the system of example 1, wherein the electrical energy is supplied to the electronic circuit at a supply voltage in a range of 0.25 V to 0.5 V.

Example 4 includes the system of example 1, wherein the signal converter includes a delta-sigma modulation analog-to-digital (DSM ADC) converter or a ring oscillator sub-circuit.

Example 5 includes the system of example 4, wherein the ring oscillator sub-circuit includes a slow ring oscillator, fast ring oscillator, and pulser.

Example 6 includes the system of example 1, wherein the electronic circuit includes a wireless transmitter to wirelessly transmit the digital data to an external device.

Example 7 includes the system of example 6, wherein the wireless transmitter includes a radio frequency (RF) antenna or an LC power oscillator.

Example 8 includes the system of example 1, wherein the first nanocomposite includes a carbon nanotube (CNT)-based mediator nanocomposite formed on a thin layer of carbon.

Example 9 includes the system of example 1, wherein the second nanocomposite includes a carboxylated-CNT/$Ag_2O$ nanocomposite.

Example 10 includes the system of example 1, wherein a maximum power point generated from the enzymatic layer correlates linearly with a concentration of the glucose or lactate that is detected.

Example 11 includes the system of example 1, wherein the enzymatic layer includes lactate (LOx) or glucose oxidase (GOx), and bovine serum albumin (BSA).

Example 12 includes the system of example 1, wherein the system is configured in an ingestible capsule, wherein the ingestible capsule comprises: a capsule housing including a curved cylindrical body encompassing a hollow interior and an opening at one end of the capsule housing to the hollow interior; a biofuel cell contingent that includes the anode and the cathode, the biofuel cell contingent contained in a first chamber within the hollow interior of the capsule housing proximate the opening; and the electronic circuit contained in a second chamber within the hollow interior of the capsule housing.

Example 13 includes the system of example 12, wherein the electronic circuit is contained in the second chamber having an area of less than 0.8 cm×1.7 cm contained within the capsule, wherein the capsule includes a height of 3.2 cm or less and a diameter of 1.1 cm or less.

In some embodiments in accordance with the present technology (example 14), an electronic device powered by biofuel cell includes an enzymatic biofuel cell to extract energy from a biological fluid that is coupled to an amplifier circuit. The enzymatic biofuel cell includes an anode disposed on a substrate, the anode including a catalyst to facilitate the conversion of an enzymatic substance in the biological fluid to a first product in an oxidative process that releases electrons captured at the anode, thereby extracting energy from the enzymatic substance, and a cathode disposed on the substrate separated from the anode, the cathode operable to reduce an oxygenated substance in the biological fluid to a second product in a chemical reduction process in which the second product gains electrons. The amplifier circuit includes a signal converter coupled to a switched or matched impedance load, where the signal converter is operable to supply electrical current from the extracted energy to the amplifier circuit to establish a supply voltage at 0.25 V to 0.4 V when the switched or matched impedance load connects the signal converter to the anode of the enzymatic biofuel cell. In some embodiments in accordance with example 14, the signal converter includes a delta-sigma modulation analog-to-digital converter (DSM ADC) operable directly from the energy extracted by the enzymatic biofuel cell; and in some embodiments, the switched or matched impedance load includes a switch coupled between the enzymatic biofuel cell and the DSM ADC to supply electrical current from the extracted energy to the amplifier circuit to establish a supply voltage at 0.25 V to 0.4 V.

Example 15 includes the electronic device of example 14, wherein the switch supplies the electrical current from the extracted energy to establish the supply voltage to the DSM ADC that is near an open-circuit voltage of the enzymatic biofuel cell such that power consumption of the circuit is less than a maximum power point (MPP) of the enzymatic biofuel cell.

Example 16 includes the electronic device of example 15, wherein the device is operable to determine a concentration of the enzymatic substance based on the MPP of the enzymatic biofuel cell.

Example 17 includes the electronic device of example 14, further including a wireless transmitter electrically coupled to the amplifier circuit.

Example 18 includes the electronic device of example 17, wherein the wireless transmitter includes a radio frequency (RF) antenna.

Example 19 includes the electronic device of example 17, wherein the enzymatic biofuel cell, the amplifier circuit and the wireless transmitter are coupled to a single substrate.

Example 20 includes the electronic device of example 17, wherein the electronic device is configured in an ingestible capsule, wherein the ingestible capsule includes a capsule housing including a curved cylindrical body encompassing a hollow interior and an opening at one end of the capsule housing to the hollow interior; the enzymatic biofuel cell contained in a first chamber within the hollow interior of the capsule housing proximate the opening; and the amplifier circuit and the wireless transmitter configured on a printed circuit board (PCB) contained in a second chamber within the hollow interior of the capsule housing.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A self-powered biosensing system for detecting an analyte, comprising:
    an electronic circuit, including a signal converter and a switched load;
    an anode, including a first nanocomposite and an enzymatic layer,
        wherein the anode is electrically coupled to an input voltage terminal of the signal converter, and configured to interact with an analyte in a fluid, the analyte including glucose or lactate;
    a cathode, including a second nanocomposite and electrically coupled to a ground voltage terminal of the electronic circuit,
        wherein an electrical energy is generated from transformation of the analyte to a derivative substance based on electrochemical reactions across the anode and cathode,
        wherein the electrical energy is stored in an electrical energy storage device during a first phase of operation, and
        wherein the electronic circuit is configured to be powered by the electrical energy stored in the electrical energy storage device during a second phase of operation;
    a first switch electrically coupled at a first node to the switched load and electrically coupled at a second node to the electrical energy storage device; and
    a second switch electrically coupled at a third node to the ground voltage terminal and electrically coupled at a fourth node to a load impedance, wherein the switched load comprises the second switch and the load impedance,
        wherein during the second phase of operation, the first switch is open and the second switch is closed,
        wherein during the second phase of operation the electronic circuit is operable to determine from the electrical energy a digital data value representative of a concentration of the analyte,
        wherein during the first phase of operation, the first switch is closed and the second switch is open, and
        wherein during the first phase of operation, the system presents a matched load at a predetermined duty ratio via periodic activation of the second switch during the second phase of operation.

2. The system of claim 1, wherein during the second phase of operation the signal converter measures a voltage representative of a maximum power point across the anode and cathode to infer the concentration of the analyte in the fluid.

3. The system of claim 1, wherein the signal converter includes a delta-sigma modulation analog-to-digital (DSM ADC) converter.

4. The system of claim 1, wherein the signal converter includes a ring oscillator sub-circuit that includes a slow ring oscillator, a fast ring oscillator, and a pulser.

5. The system of claim 1, wherein the electronic circuit includes a wireless transmitter to wirelessly transmit the digital data to an external device.

6. The system of claim 5, wherein the wireless transmitter includes a radio frequency (RF) antenna or an LC power oscillator.

7. The system of claim 1, wherein the first nanocomposite includes a carbon nanotube (CNT)-based mediator nanocomposite formed on a layer of carbon.

8. The system of claim 1, wherein the second nanocomposite includes a carboxylated CNT and Ag2O nanocomposite.

9. The system of claim 1, wherein maximum power point values generated from the enzymatic layer correlate linearly with a concentration of the glucose or lactate that is detected.

10. The system of claim 1, wherein the enzymatic layer includes lactate (LOx) or glucose oxidase (GOx), and bovine serum albumin (BSA).

11. The system of claim 1, wherein the system is configured in an ingestible capsule, wherein the ingestible capsule comprises:

a capsule housing including a curved cylindrical body encompassing a hollow interior and an opening at one end of the capsule housing to the hollow interior;

a biofuel cell contingent that includes the anode and the cathode, the biofuel cell contingent contained in a first chamber within the hollow interior of the capsule housing proximate the opening; and the electronic circuit contained in a second chamber within the hollow interior of the capsule housing.

12. The system of claim 11, wherein the electronic circuit is contained in the second chamber having an area of less than 0.8 cm×1.7 cm contained within the capsule, wherein the capsule includes a height of 3.2 cm or less and a diameter of 1.1 cm or less.

13. The system of claim 1, wherein the first switch electrically coupled to the input voltage terminal and electrically coupled to a power supply terminal for supplying power to the electronic circuit.

14. The system of claim 1, wherein the electrical energy stored in the electrical energy storage device is supplied to the electronic circuit at a supply voltage in a range of 0.25 V to 0.5 V.

15. The system of claim 1, wherein the second phase of operation is performed with a duty cycle lower than the first phase of operation.

16. The system of claim 1, wherein the predetermined duty ratio is at a 1% or less duty cycle.

* * * * *